United States Patent [19]

Arvidsson et al.

[11] Patent Number: 4,937,346

[45] Date of Patent: Jun. 26, 1990

[54] PHENYL-AZACYKLOALKANES

[75] Inventors: Folke L. Arvidsson, Upsala; Per A. E. Carlsson, Torild Wulffsgatan 50, S-413 19 Göteborg; Uli A. Hacksell, Uppsala; John S. M. Hjorth, Göteborg; Per L. Lindberg, Askim; John L. G. Nilsson, Tullinge; Domingo Sanchez, Floda; Nils U. E. Svensson, Brunna; Hakan V. Wikstrom, Göteborg, all of Sweden

[73] Assignee: Per Arvid Emil Carlsson, Sweden

[21] Appl. No.: 126,916

[22] Filed: Nov. 30, 1987

Related U.S. Application Data

[60] Division of Ser. No. 656,616, Oct. 1, 1984, and a continuation-in-part of Ser. No. 480,089, Mar. 30, 1983, abandoned, which is a continuation-in-part of Ser. No. 461,504, Jan. 27, 1983, abandoned, which is a continuation of Ser. No. 213,633, Dec. 5, 1980, Pat. No. 4,426,386.

[30] Foreign Application Priority Data

Dec. 5, 1979 [SE] Sweden ............................ 7910026
Mar. 30, 1982 [SE] Sweden ............................ 8202023
Sep. 30, 1983 [SE] Sweden ............................ 8305362

[51] Int. Cl.$^5$ .................. C07D 211/18; C07D 211/32; C07D 211/54; C07D 211/22
[52] U.S. Cl. .................................... 546/232; 546/233; 546/238; 546/240
[58] Field of Search ................ 546/232, 233, 238, 240

[56] References Cited

U.S. PATENT DOCUMENTS 2,892,842  6/1959  McElvain .......................... 546/232
4,426,386  1/1984  Arvidsson et al. ................ 546/232

OTHER PUBLICATIONS

Roberts, et al., Basic Principles of Organic Chemistry, 2nd Ed., W. A. Benjamin, Inc., Menlo Park, Calif., (1977).
Bulletin de la Societe Chimique de France, 1968, No. 3, pp. 1000–1007.
J. Med. Chem., 1981, 24, pp. 1475–1482.

Primary Examiner—Mary C. Lee
Assistant Examiner—Robert C. Whittenbaugh
Attorney, Agent, or Firm—Brumbaugh, Graves, Donohue & Raymond

[57] ABSTRACT

Compound of the formula

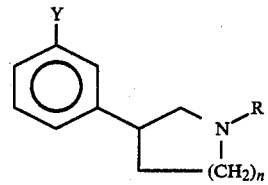

wherein n is 1 or 2, Y is OH, $R^1COO-$, $R^2R^3NCOO-$ or $R^4O$ whereby $R^1$ is an alkyl group, or a possibly substituted phenyl group, $R^2$ is an alkyl, phenethyl, or benzyl or phenyl group, $R^3$ is H or an alkyl group and $R^4$ is an allyl or benzyl group, and R is an alkyl, hydroxyalkyl, dimethylaminoalkyl or methylthioalkyl group or alkenyl group, processes for their preparations and methods of treatment employing such compounds. The compounds are useful for therapeutic purposes, especially for treatment of disorders in the central nervous system.

8 Claims, No Drawings

PHENYL-AZACYKLOALKANES

TECHNICAL FIELD

This application is a divisional of U.S. application Ser. No. 656,616, filed Oct. 1, 1984, which is a continuation-in-part of U.S. application Ser. No. 480,089, filed Mar. 30, 1983 (now abandoned), which is a continuation-in-part of U.S. application Ser. No. 461,504, filed Jan. 27, 1983 (now abandoned), which is a continuation of U.S. application Ser. No. 213,633, filed Dec. 5, 1980 (now U.S. Pat. No. 4,426,386).

The present invention is related to new substituted phenylazacycloalkanes, and the pure enantiomers, to processes for preparing such compounds as well as to pharmaceutical preparations thereof and methods of treatment employing such compounds.

An object of the invention is to provide compounds for therapeutic use, especially having a therapeutic activity in the central nervous system.

BACKGROUND ART

In Chemical Abstracts 69: 867765 (citing Julia, M. et al., Bull. Soc. Chim. Fr. 1968, (3), 1000-7) compounds under the general formula

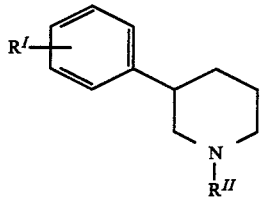

are described. Among the compounds mentioned are compounds wherein $R^I$ represents m-OCH$_3$ and $R^{II}$ represents H, CH$_3$, C$_2$H$_5$, CH$_2$C$_6$H$_5$, CH$_2$CH$_2$C$_6$H$_5$ or CH$_2$CH$_2$C$_6$H$_4$NO$_2$(p) and wherein $R^I$ represents m—OH and $R^{II}$ represents CH$_2$CH$_2$C$_6$H$_5$ or CH$_2$CH$_2$C$_6$H$_4$NO$_2$(p). Said compounds were prepared for investigation of pharmacological properties.

Swiss Patent No. 526,536 describes compounds under the formula

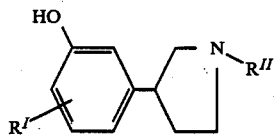

wherein $R^I$ represents H or OH and $R^{II}$ represents H. The compounds are claimed to have useful pharmacological properties especially as broncholytic agents.

DE Offenlegungschrift 2 621 536 describes compounds of the formula

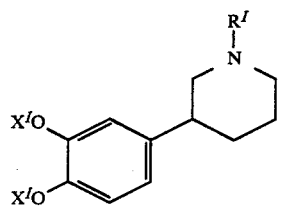

wherein $X^I$ is hydrogen or an acyl group and $R^I$ is an alkyl, alkenyl or phenylalkyl group The compounds are claimed to have dopaminergic properties.

EP-Al-0030526 and Hacksell et al. in J. Med. Chem., vol. 24, p. 1475-1482 (1981) describe compounds of the formula

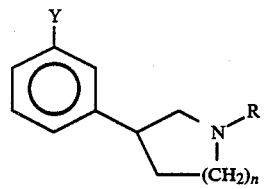

wherein n is 1 or 2, Y is OH, R$^1$COO, R$^2$R$^3$NCOO—or R$^4$O whereby R$^1$ is an alkyl group having 1-5 carbon atoms or a possibly substituted phenyl group, R$^2$ is an alkyl group having 1-5 carbon atoms, a phenethyl, benzyl or phenyl group, R$^3$ is H or an alkyl group having 1-5 carbon atoms, and R$^4$ is an allyl or benzyl group, and R is an alkyl group having 1-5 carbon atoms, a hydroxyalkyl, dimethylaminoalkyl or methylthioalkyl group having 2-6 carbon atoms in the alkyl part and having the heteroatom bound in a position other than the 1 position, or an alkenyl group having 3-5 carbon atoms other than a 1-alkenyl group, as bases and pharmaceutically acceptable acid addition salts thereof, which compounds are potent neuropharmacological agents. Thus said compounds are active as presynaptic dopamine receptor agonists when administered to animals including man. Said compounds are thus useful for treatment of disorders in the central nervous system, especially psychotic disorders in man.

In particular compounds of the above formula wherein R represents n-propyl are described. EP-Al-0030526 refers to and covers in general the pure enantiomers as well as mixtures thereof. However, the enantiomers are not specifically disclosed.

In Acta Pharmaceutica Suecica Suppl. 1983:1 p. 130-137 and 145-153 the pharmacological properties of the (−) and (+) enantiomers of the compound

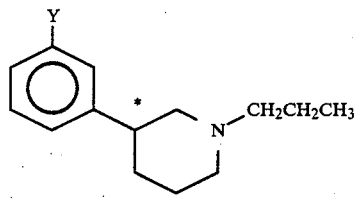

are described.

In European Patent Application No. 83850084.1, enantiomers of compounds of the formula

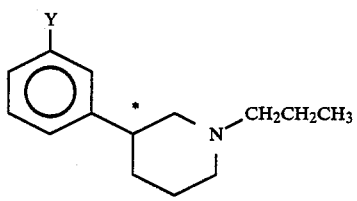

are described wherein Y is OH, R$^1$COO, R$^2$R$^3$NCOO or R$^4$O. In compounds wherein Y is R$^2$R$^3$NCOO R$^2$ is hydrogen, an alkyl group having 1-5 carbon atoms, a phenethyl, benzyl or phenyl group which may be mono- or disubstituted in the aromatic part with a methyl, methoxy, hydroxy, nitro or cyano group or a halogen, $R^3$ is H, an alkyl group having 1 to 5 carbon atoms or a phenyl group or $R^2$ and $R^3$ together with the nitrogen atom form a 5, 6 or 7 membered ring that may contain 1 to 3 double bonds and/or 1 or 2 further heteroatoms selected from N, O and S. Specifically described in either of the two European patent applications above is i.a. a compound wherein Y is

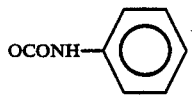

DISCLOSURE OF INVENTION

According to the present invention it has been found that novel compounds of the formula

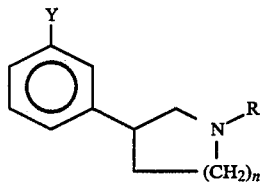

I wherein n is 1 or 2, Y is OH, $R^1COO$, $R^2R^3NCOO—$ or $R^4O$ whereby $R^1$ is an alkyl group having 1-5 carbon atoms or a possibly substituted phenyl group, $R^2$ is an alkyl group having 1-5 carbon atoms, a phenethyl, benzyl or phenyl group, $R^3$ is H or an alkyl group having 1-5 carbon atoms, and $R^4$ is an allyl or benzyl group, and R is an alkyl group having 1-5 carbon atoms, a hydroxyalkyl, dimethylaminoalkyl or methylthioalkyl group having 2-6 carbon atoms in the alkyl part and having the heteroatom bound in a position other than the 1 position, an alkenyl group having 3-5 carbon atoms other than a 1-alkenyl group, as bases and pharmaceutically acceptable acid addition salts thereof, are potent neuropharmacological agents. Thus said compounds are active as presynaptic dopamine receptor agonists when administered to animals including man. The compounds are thus useful for treatment of disorders in the central nervous system, especially psychotic disorders in man. Further, among the compounds of the invention are compounds having a positive inotropic cardiac effect, substantially lacking chronotropic effect. Such compounds are useful for treatment of cardiac insufficiency.

An alkyl group may be a straight alkyl group or a branched alkyl group having at least 3 carbon atoms.

A possibly substituted phenyl group $R^1$ may be a phenyl, 2,6-dimethylphenyl or 3- or 4-hydroxyphenyl group or a 3- or 4-alkanoyloxyphenyl group with the formula

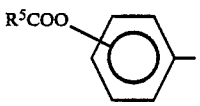

wherein $R^5$ is an alkyl group having 1-6 carbon atoms.

According to the present invention it has also been found that the pure enantiomeric forms of compounds of the formula

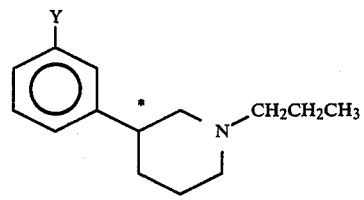

(a) (I)

wherein Y is OH, $R^1COO$, $R^2R^3NCOO—$ or $R^4O$ whereby $R^1$ is an aliphatic hydrocarbon residue having 1-17 carbon atoms, a phenyl, 2,6-dimethylphenyl or 3- or 4-hydroxyphenyl group or a 3- or 4-alkanoyloxyphenyl group with the formula

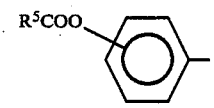

wherein $R^5$ is an alkyl group having 1-6 carbon atoms, or $R^1$ is a group

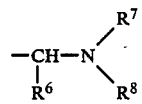

wherein $R^6$ is hydrogen, an alkyl group having 1 to 5 carbon atoms or a phenyl group, $R^7$ is hydrogen, an alkyl group having 1 to 5 carbon atoms or an acyl group and $R^8$ is hydrogen or an alkyl group having 1 to 5 carbon atoms, $R^2$ is hydrogen, an alkyl group having 1 to 5 carbon atoms, a phenethyl, benzyl or phenyl group which may be mono- or disubstituted in the aromatic part with a methyl, methoxy, hydroxy, nitro or cyano group or a halogen, $R^3$ is H, an alkyl group having 1 to 5 carbon atoms or a phenyl group or $R^2$ and $R^3$ together with the nitrogen atom form a 5, 6 or 7 membered ring that may contain 1 to 3 double bonds and/or 1 to 2 further heteroatoms selected from N, O and S, and $R^4$ is an allyl or benzyl group, said enantiomer having the same absolute configuration at the asymmetric carbon atom(*) as that of the (—)-enantiomer of the compound of formula 1 wherein Y is OH, as bases and pharmaceutically acceptable acid addition salts thereof, possess unexpected valuable therapeutical properties in addition to those previously described.

The (—)-enantiomer of the compound of the formula 1 wherein Y is OH is the levo rotameric form. Compounds of the invention having Y other than OH have the same absolute configuration as said (—)-enantiomer, it being understood that said latter compounds are not necessarily the (—) or levo rotameric forms.

In the pure enantiomers of the invention Y is in particular OH, $R^1COO$, $R^2R^3NCOO—$ or $R^4O$ whereby $R^1$ is an alkyl group having 1-5 carbon atoms or a phenyl, 2,6-dimethylphenyl or 3- or 4-hydroxyphenyl group or a 3- or 4-alkanoyloxyphenyl group with the formula

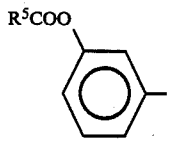

wherein $R^5$ is an alkyl group having 1-6 carbon atoms $R^2$ is an alkyl group having 1-5 carbon atoms, a phenethyl, benzyl or phenyl group, $R^3$ is H or an alkyl group having 1-5 carbon atoms, and $R^4$ is an allyl or benzyl group. By X-ray crystallography the absolute configuration of the (−)-enantiomer of the compound of formula 1 wherein Y is OH has been determined to be the S configuration. Thus, the compounds of the invention according to formula 1 all have S configuration.

An alkyl group may be a straight alkyl group or a branched alkyl group having at least 3 carbon atoms. An acyl group $R^7$ is a formyl, acetyl, benzoyl, methoxycarbonyl, phenoxycarbonyl or benzyloxycarbonyl group. An aliphatic hydrocarbon residue $R^1$ may be saturated or unsaturated.

According to the present invention it has also been found that compounds of the formula

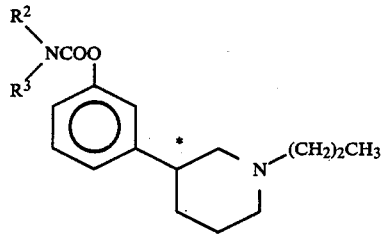

b I wherein $R^2$ is n-propyl, isopropyl, tert. butyl or one of the groups

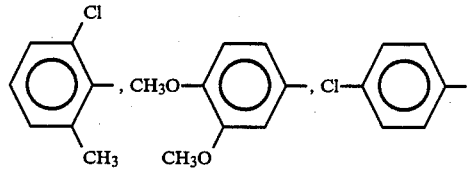

and $R^3$ is hydrogen; or $R^2$ and $R^3$ are each a n-propyl, isopropyl or tert. butyl group; or $R^2$ and $R^3$ together form the group —$(CH_2)_5$— as bases and pharmaceutically acceptable acid addition salts thereof possess unexpected valuable therapeutical properties.

Symbols for numbers, atoms or groups referred to below have the broadest meaning previously assigned unless specified otherwise.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic and benzoic acid. These salts are readily prepared by methods known in the art.

In a restricted embodiment the invention is related to compounds of the formula I above wherein n is 1 or 2, Y is OH, $R^1COO$— or $R^2R^3NCOO$—, whereby $R^1$ is an alkyl group having 1-5 carbon atoms, or a phenyl group, and $R^2$ is an alkyl group having 1-5 carbon atoms, a phenethyl, benzyl or phenyl group, and $R^3$ is H or an alkyl group having 1-5 carbon atoms, and R is an alkyl group having 1-5 carbon atoms, a hydroxyalkyl group having 2-6 carbon atoms in the alkyl part other than a 1-hydroxyalkyl group, an alkenyl group having 3-5 carbon atoms other than a 1-alkenyl group.

According to a preferred embodiment the invention is related to compounds of the formula I wherein n is 2 and Y and R are as specified above.

Preferred compounds are those wherein Y is OH or $R^1COO$ or $R^4O$. Further preferred are compounds wherein R is an alkyl group having 3-5 carbon atoms.

In another preferred embodiment the invention is related to pure enantiomeric compounds of the formula 1 as defined above wherein Y is OH, $R^1COO$— or $R^2R^3NCOO$—, whereby $R^1$, $R^2$ and $R^3$ are as defined above.

Compounds to be specifically mentioned are:
(−)-3-(3-Hydroxyphenyl)-N-n-propylpiperidine,
(−)-N-n-propyl-3-[3-(4-pivaloyloxybenzoyloxy)-phenyl]piperidine,
(−)-N-n-propyl-3-(3-allyloxyphenyl)piperidine,
(−)-3-(3-decanoyloxyphenyl)-1-propylpiperidine,
S-3-(3-pivaloyloxyphenyl)-N-n-propylpiperidine,
S-3-(3-acetoxyphenyl)-N-n-propylpiperidine,
S-3-(3-benzyloxyphenyl)-N-n-propylpiperidine, S-3-(3-N', N'-dimethylcarbamoyloxyphenyl)-N-n-propylpiperidine,
S-3-(3-N'-phenylcarbamoyloxyphenyl)-N-n-propylpiperidine,
and S-3-(3-N'-benzyloxycarbonylalanylphenyl)-N-n-propylpiperidine.

The compounds of the invention contain an asymmetric carbon atom in the heterocyclic ring moiety. The therapeutic properties of the compounds may to a greater or lesser degree be ascribed to either or both of the two enantiomers occurring. Thus the pure enantiomers as well as mixtures thereof are within the scope of the invention.

The invention takes into consideration that compounds which structurally deviate from the formula I, after administration to a living organism, may be transformed to a compound of the formula I and in this structural form exert their effects. This consideration is a further aspect of the invention. Likewise, certain compounds of formula I may be metabolized into other compounds of formula I before exerting their effect. Compounds of the invention wherein Y is $R^1COO$. $R^2R^3NCOO$ or $R^4O$ are thus believed to exert their main activity after metabolism to compounds wherein Y is OH.

In particular, the most valuable therapeutical properties have been found to reside in compounds having S configuration at the asymmetric carbon atom(*) which thus constitute a preferred embodiment of the invention.

METHODS OF PREPARATION

The compounds of the invention may be obtained by one of the following methods constituting a further aspect of the invention.

I. New Substituted Phenylazacycloalkanes (a) An ether or ester of the formula

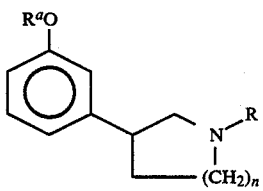

II wherein $R^a$ represents a hydrocarbon or acyl residue, preferably an alkyl group having 1–5 carbon atoms, or an alkylcarbonyl group having 2–6 carbon atoms, and n and R are as defined above, may be cleaved to form a compound of formula I wherein Y is a hydroxy group.

When $R^a$ is a hydrocarbon residue the cleavage may be carried out by treating the compound of the formula II with an acidic nucleophilic reagent such as aqueous HBr, or HI, HBr/CH$_3$COOH, BBr$_3$, AlCl$_3$, pyridine-HCl or (CH$_3$)$_3$ SiI, or with a basic nucleophilic reagent such as CH$_3$C$_6$H$_4$—S$^-$ or $C_2H_5$—S$^{3}$¹.

When $R^a$ is an acyl residue the cleavage may be carried out by hydrolysis in an aqueous acid or base or by reduction, preferably by LiAlH$_4$.

(b) In a compound of the formula

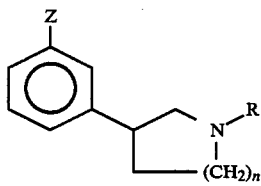

III wherein Z represents SO$_3$H, Cl or NH, a hydroxy group may be substituted for the group Z to the formation of a compound of formula I wherein Y represents a hydroxy group. When Z is SO$_3$H or Cl said reaction may be carried out by treatment with a strong alkali under heating, suitably with an alkali melt such as KOH when Z is SO$_3$H, and with a strong aqueous alkali such as NaOH or KOH when Z is Cl. When Z is NH$_2$ the reaction may be carried out by treatment with aqueous nitrous acid to the formation of an intermediate diazonium compound which is then subjected to hydrolysis in water.

(c) A compound of the formula I

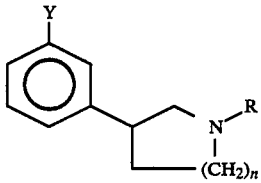

I wherein Y is OH and R is other than hydroxyalkyl may be converted into a compound of the same formula wherein Y is R$^1$COO, R$^2$R$^3$NCOO or R$^4$O by treating the first mentioned compound with an appropriate carboxylic acid halide R$^1$COX or anhydride (R$^1$CO)$_2$O or with an appropriate carbamoyl halide R$^2$R$^3$NCOX or isocyanate R$^2$NCO in the presence of a base such as triethylamine or pyridine or an acid such as H$_2$SO$_4$or CF$_3$COOH or with an appropriate allyl or benzyl halide R$^4$X in the presence of a base such as triethylamine, pyridine or potassium t-butoxide. X represents a halogen, preferably Cl or Br.

Alternatively, when conversion of Y=OH into R$^1$COO is intended and R$^1$is

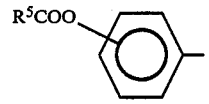

a compound of formula I wherein Y is OH may first be converted to a compound of formula I wherein Y is

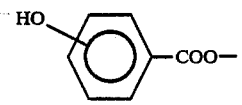

which is then treated with an appropriate carboxylic acid halide R$^5$COX or anhydride (R$^5$CO)$_2$O is the presence of a base or an acid.

(d) A compound of the formula

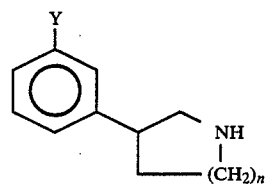

may be converted into a compound of formula I by alkylation of the nitrogen atom with an appropriate alkylating agent. Thus, the starting compound may be treated with an alkyl, hydroxyalkyl, dimethylaminoalkyl, methylthioalkyl, alkenyl or benzyl halide or tosylate RX$_1$, wherein X$^1$represents Cl, Br, I or

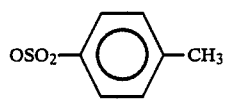

in an organic solvent such as acetonitrile or acetone and in the presence of a base such as K$_2$CO$_3$or NAOH, or the starting compound may be treated with a carboxylic acid NaBH$_4$ complex R$^b$COOH-NaBH$_4$, wherein R$^b$ is defined by the relation R$^b$-CH$_2$-equals R. To the formation of a compound of formula I wherein R is CH$_3$, which is not obtainable by the last-mentioned reaction, the alkylation reaction may be carried out by treatment with a formaldehyde —Na(CN)BH$_3$ mixture. To the formation of a compound of formula I wherein R is hydroxyalkyl, dimethylaminoalkyl or methylthioalkyl the synthesis may also be carried out by alkylation with an appropriate dihaloalkane giving a monohaloalkyl derivative of I followed by acid or alkaline hydrolysis and reaction with dimethylamine or CH$_3$S$^\theta$. Especially, to the formation of a compound of formula I wherein R is 2-hydroxyalkyl, the alkylation may also be carried out by reaction with a 1,2-epoxyalkane.

(e) An amide- or imida- containing compound of the formula

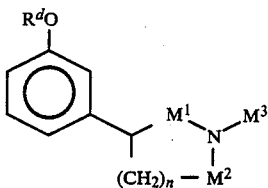

IV wherein $M^1$ and $M^2$ are the same or different and each represents —$CH_2$— or

C=O, and $M^3$ is $$-\underset{\underset{O}{\|}}{C}-R^c$$

when $M^1$ and $M^2$ are both —$CH_2$—, and in other case $M^3$ is R. $R^c$ is H, an alkyl or alkoxyl group containing 1-4 carbon atoms, a hydroxyalkyl, dimethylaminoalkyl or methylthioalkyl group containing 1-5 carbon atoms, or an alkenyl group containing 2-4 carbon atoms, and $R^d$ is H, $R^1CO$, allyl or benzyl may be converted into a compound of the formula I wherein Y is a hydroxy, allyl or benzyl group by reduction of the amide or imide function, and the ester function $R^1COO$ if present. Thus the compound of formula IV may be treated with a reducing agent, preferably a hydride reducing agent such as $LiAlH_4$ or $BH_3$ in an etheral solvent or a metal reducing agent such as Na in an alcoholic solvent such as n-butanol.

(f) A compound of the formula

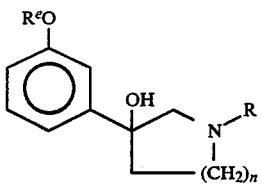

V wherein $R^e$ is H or benzyl and wherein R is an alkyl or hydroxyalkyl, dimethylaminoalkyl or methylthioalkyl group as further defined above, may be converted either by direct reduction or by first elimination of the tertiary alcohol to an intermediary 1-cycloalkenyl compound and then reduction into a compound of formula I wherein Y is Oh and R is as just defined. The reduction may preferably be carried out by catalytic hydrogenation with a catalyst such as Pd or $PtO_2$, and the elimination reaction by heating in the presence of an acid.

(h) A compound of the formula

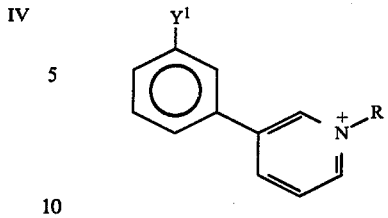

VII wherein $Y^1$ is benzyloxy or Y, wherein Y is as originally defined, however, other than O-allyl, and R is an alkyl group containing 1-5 carbon atoms or a hydroxyalkyl, dimethylaminoalkyl or methylthioalkyl group containing 2-6 carbon atoms and having the heteroatom bound in a position other than the 1-position, may be converted by reduction into the corresponding compound of formula I wherein n is 2. When $Y^1$ is benzyloxy a compound of formula I wherein Y is OH is obtained. The reduction may preferably be carried out by catalytic hydrogenation using a catalyst such as $PtO_2$, or by reduction with $NaHB_4$ followed by catalytic hydrogenation.

(i) A compound according to the formula

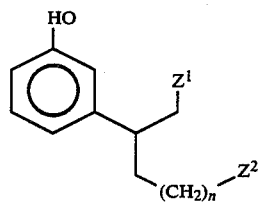

VIII wherein one of the group $Z^1$ and $Z^2$ is a leaving group, X and the other is NHR, or $Z^1$ and $Z^2$ are both leaving groups X, and X is a leaving group such as Cl, Br, I or $-OSO_2C_6H_4CH_3$, may be converted to a compound of formula I wherein Y is OH by treating the compound of formula VIII, or when one of $Z^1$ and $Z^2$ is NHR an acid addition salt thereof, with a base such as $(C_2H_5)_3N$ or $K_2CO_3$, whereby the compound of formula VIII is treated together with an equivalent amount of an amine R—$NH_2$ or an acid addition salt thereof when $Z^1$ and $Z^2$ are both X. The conversion is carried out in a solvent such as tetrahydrofuran, dioxan or acetonitrile, if necessary with simultaneous or subsequent heating of the mixture.

Free bases formed may subsequently be converted into their acid addition salts, and acid addition salts formed may subsequently be converted into the corresponding bases or other acid addition salts.

II. New Enantiomers of substituted phenylazacycloalkanes

The compounds of the invention may be obtained by one of the following methods constituting a further aspect of the invention.

(j) A pure enantiomer of an ether or ester of the formula

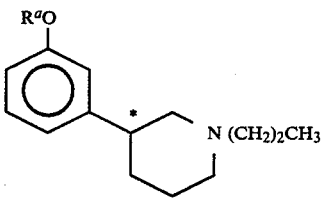

a (2)

having the appropriate absolute configuration at the asymmetric carbon atom(*), wherein $R^a$ represents a hydrocarbon or acyl residue, preferably an alkyl group having 1–5 carbon atoms, or an alkylcarbonyl group having 2–6 carbon atoms defined above, may be cleaved to form the compound of formula 1 wherein Y is a hydroxy group, in the desired (—)-enantiomeric form.

When $R^a$ is a hydrocarbon residue the cleavage may be carried out by treating the compound of formula 2 with an acidic nucleophilic reagent such as aqueous HBr, or HI, HBr/CH$_3$COOH, BBr$_3$, AlCl$_3$, pyridine—HCl or (CH$_3$)$_3$ SiI, or with a basic nucleophilic reagent such as CH$_3$C$_6$H$_4$—S$^-$ or $C_2$H$_5$—S$^-$.

When $R^a$ is an acyl residue the cleavage may be carried out by hydrolysis in an aqueous acid or base or by reduction, preferably by LiAlH$_4$.

(k) In a pure enantiomer of a compound of the formula

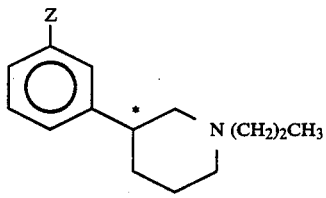

a (3)

having the appropriate absolute configuration at the asymmetric carbon atom(*), wherein Z represents SO$_3$H, Cl or NH$_2$, a hydroxy group may be substituted for the group Z to the formation of a compound of formula 1 wherein Y represents a hydroxy group and in the desired (—)-enantiomeric form. When Z is SO$_3$H or Cl said reaction may be carried out by treatment with a strong alkali under heating, suitably with an alkali melt such as KOH when Z is SO$_3$H, and with a strong aqueous alkali such as NaOH or KOH when Z is Cl. When Z is NH$_2$ the reaction may be carried out by treatment with aqueous nitrous acid to the formation of an intermediate diazonium compound which is then subjected to hydrolysis in water.

(l) The (—)-enantiomeric form of the compound of formula 1

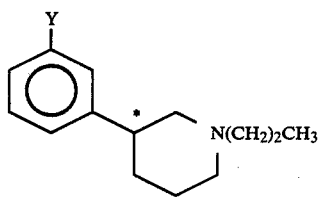

a(1)

wherein Y is OH may be converted into a compound of the same formula and the same absolute configuration at the asymmetric carbon atom(*) wherein Y is R$^1$COO, R$^2$R$^3$NCOO or R$^4$O by treating the first mentioned compound with an appropriate carboxylic acid halide R$^1$COX or anhydride (R$^1$CO)$_2$O or with an appropriate carbamoyl halide R$^2$R$^3$NCOX or isocyanate R$^2$NCO in the presence of a base such as triethylamine or pyridine or an acid such as H$_2$SO$_4$ or CF$_3$COOH or with an appropriate allyl or benzyl halide R$^4$X in the presence of a base such as triethylamine, pyridine or potassium t-butoxide. X represents a halogen, preferably Cl or Br.

Alternatively, when conversion of Y=OH into R$^1$COO is intended and R$^1$is

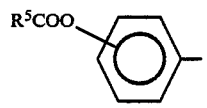

a compound of formula 1 wherein Y is OH may first be converted to a compound of formula 1 wherein Y is

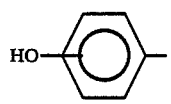

COO$^-$ which is then treated with an appropriate carboxylic acid halide R$^5$COX or anhydride (R$^5$CO)$_2$O in the presence of a base or an acid.

(m) A pure enantiomer of a compound of the formula

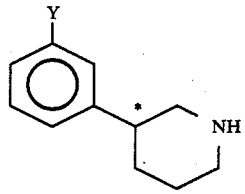

a(4)

having the appropriate absolute configuration may be converted into a compound of formula 1 having the desired absolute configuration at the asymmetric carbon atom(*) by alkylation of the nitrogen atom with an appropriate alkylating agent. Thus the starting compound may be treated with a n-propyl halide or tosylate RX$^1$, wherein X$^1$ represents Cl, Br, I or OSO$_2$

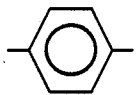

CH$_3$ in an organic solvent such as acetonitrile or acetone and in the presence of a base such as K$_2$CO$_3$ or NaOH, or the starting compound may be treated with a n-propionic acid NaBH$_4$ complex.

(n) A pure enantiomer of a carbonyl compound of the formula

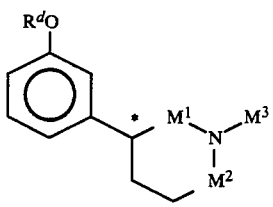 a(5)

having the appropriate absolute configuration, wherein $M^1$ and $M^2$ are the same or different and each represents —$CH_2$— or

and the dashed lines represent bonds, one of which, when adjacent to a group

may be open and replaced by hydrogen atoms, and $M^3$ is

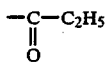

when $M^1$ and $M^2$ are both —$CH_2$—, and in other cases $M^3$ is n-$C_3H_7$, and $R^d$ is H or $R^1CO$, may be converted into a compound of the formula 1 having the desired absolute configuration at the asymmetric carbon atom(*) and wherein Y is a hydroxy, allyloxy or benzyloxy group by reduction of the amide or imide function, and the ester function $R^1COO$ if present.

Thus the compound of formula 5 may be treated with a reducing agent, preferably a hydride reducing agent such as $LiAlH_4$ or $BH_3$ in an etheral solvent or a metal reducing agent such as Na in an alcoholic solvent such as n-butanol when ring closure is not required When one of the dashed lines in formula 5 represents an open bond, the reduction comprises a ring closure in a compound of the formula

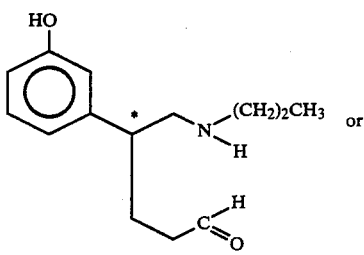

and may be done by catalytic hydrogenation.

(o) A compound of the formula

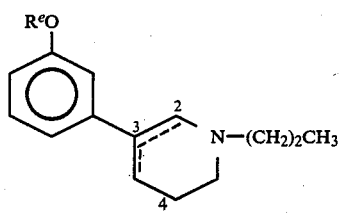 a(6)

with either a $C_2$-$C_3$ or a $C_3$-$C_4$ double bond and wherein $R^e$ is H or benzyl may be converted by reduction into a compound of formula 1 wherein Y is OH and having the desired (−)-enantiomeric form. The reduction may preferably be carried out by catalytic hydrogenation with an appropriate chiral homogenous phase catalyst such as a Rh-complex with chiral phosphines. If required, the product may be purified to obtain only the desired enantiomer in a pure form.

(p) A pure enamtiomer of a compound according to the formula

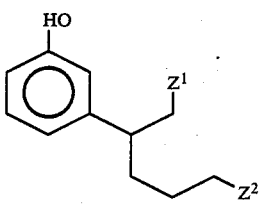 a(7)

having the appropriate absolute configuration, wherein one of the group $Z^1$ and $Z^2$ is a leaving group X and the other is $NH(CH_2)_2CH_3$ or $Z^1$ and $Z^2$ are both leaving groups X, and X is a leaving group such as Cl, Br, I or —$OSO_2C_6H_4CH_3$, may be converted to a compound of formula 1 wherein Y is OH and having the desired (−)-enantiomeric form by treating the compound of formula 7, or when one of $Z^1$ and $Z^2$ is $NH(CH_2)_2 CH_3$ an acid addition salt thereof, with a base such as ($C_2H_5$)$_3$N or $K_2CO_3$, whereby the compound of formula 7 is treated together with an equivalent amount of an amine $CH_3(CH_2)_2$—$NH_2$ or an acid addition salt thereof when $Z^1$ and $Z^2$ are both X. The conversion is carried out in a solvent such as tetrahydrofuran, dioxane or acetonitrile, if necessary with simultaneous or subsequent heating of the mixture.

(q) A racemic mixture or a mixture partly enriched on one of the enantiomers of a compound of formula

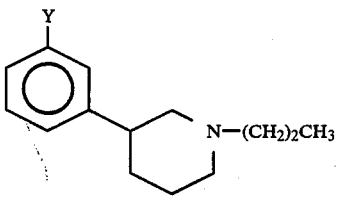
a(1)

may be subjected to a enantiomeric separation to obtain the desired enantiomer of compound 1. This may be done by methods known in the art. These methods include recrystallization of diastereomeric salts with pure enantiomers of acids such as tartaric acid, O,O'-dibenzoyltartaric acid, mandelic acid and camphor-10-sulphonic acid.

Free bases formed may subsequently be converted into their acid addition salts, and acid addition salts formed may subsequently be converted into the corresponding bases or other acid addition salts.

(r) A compound of the formula

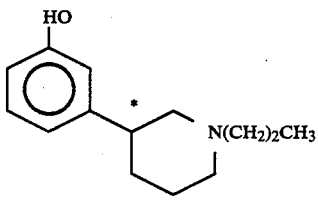
bII may be converted into a compound of formula bI by treating the first-mentioned compound with an appropriate carbamic acid derivative $R^2R^3NCOX$ or aminoformaldehyde $R^2R^3NCOH$ or isocyanate $R^2NCO$ or isocyanide $R^2N\equiv C$, whereby X represents a leaving group such as a halogen preferably Cl or Br or a metal sulfite $SO_3$ Me or the group $R^2R^3N$ The reaction with a carbamoyl halide or isocyanate is done in the presence of a base such as triethylamine or pyridine or an acid such as $H_2SO_4$ or $CF_3COOH$. The reaction with the isocyanide is done in the presence of a halogen or halogen generator such as $Br_2$, $Cl_2$ or N-bromo-succinimide. The reaction with the aminoformaldehyde may be carried out in the presence of an oxidant such as lead tetraacetate.

The isocyanate $R^2NCO$ may be added as such or formed in situ as described below.

Compound bII may be present in the form of the phenol or a metal salt thereof e.g., the sodium salt.

When X represents the group $R^2R^3N$ the reaction is carried out at an elevated pressure and temperature.

(s) A compound of the formula

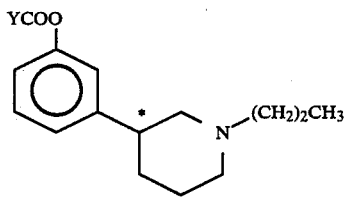
bIII wherein Y is a leaving group obtainable by reaction of phosgene or a phosgene derivative with a phenol of formula bII above, may be reacted with an amine of the formula $R^2R^3NH$ to the formation of a compound of formula bI Examples of phosgene derivatives are

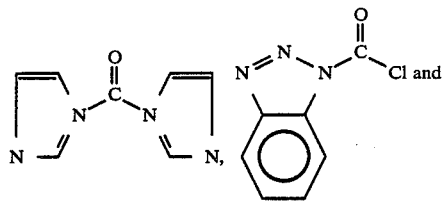

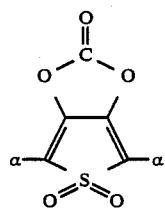

wherein $\phi$ is a phenyl group. Examples of groups Y are thus chlorine or a group derived from the phosgene derivative employed.

(t) A compound of the formula

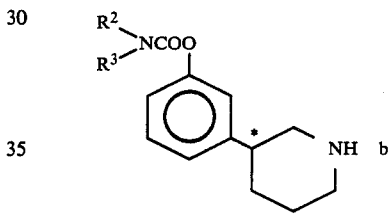
V may be converted into a compound of formula bI by alkylation of the nitrogen atom with an appropriate alkylating agent. Thus the starting compound may be treated with a n-propyl halide or tosylate $RX^1$, wherein $X^1$ represents Cl, Br, I or

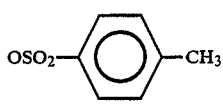

in an organic solvent such as acetonitrile or acetone and in the presence of a base such as $K_2CO_3$ or NaOH, or the starting compound may be treated with a n-propionic acid $NaBH_4$ complex.

When possible and desired a reactant may be inserted as a salt, such as a phenolic metal salt or a quaternary ammonium acid addition salt, in the place of the phenol or amine described above.

To obtain a pure enantiomer of a compound of formula bI, a racemic mixture partly enriched on one of the enantiomers of a compound of the formula I may subsequently be subjected to enantiomeric separation to obtain the desired enantiomer of compound bI. This may be done by methods known in the art. These methods include recrystallization of diastereomeric salts with pure enantiomers of acids such as tartaric acid, O,O-dibenzoyltartaric acid, mandelic acid and camphor-10-sulphonic acid.

The above methods are equally useful for preparing compounds described in European Patent Application No. 83850084.1 as presented above wherein Y is $R^2R^3NCOO$. A further embodiment of the present invention is thus preparation of comoounds described in the above-identified patent application by one of the above methods.

PREPARATION OF STARTING MATERIALS

Starting materials for the methods of preparation described above may be obtained by several methods known in Section I in the art or described below.

The starting material for method (a) according to formula II above may be prepared by one of the following methods:

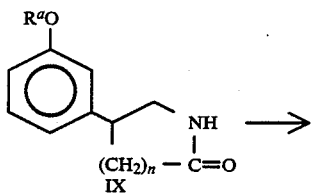
(A1)

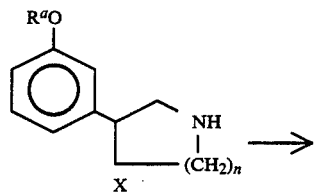

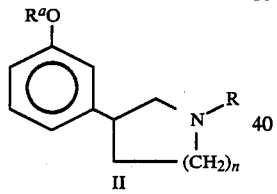

A compound of formula IX, wherein $R^a$ is an alkyl group having 1-5 carbon atoms, is reduced e.g. with LiAlH$_4$. In the compound X formed, a group R may then be introduced in analogy with the procedure of method (d) above or by modification of the first step in analogy with method (e) above.

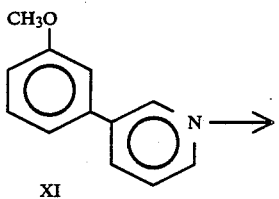
(A2)

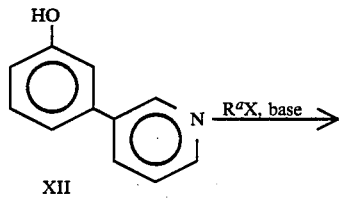

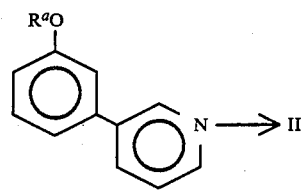

In a compound of formula XI, obtainable by method (E2) below, the methoxy group is split off with HBr, whereupon a protective group $R^a$ being an alkyl group having 1-5 carbon atoms or an acyl group having 2-6 carbon atoms, is substituted in the hydroxy group by reaction with a halide $R^aX$ in the presence of a base. The compound thus formed is then hydrogenated to the formation of a compound of formula II wherein n is 2 and $R^a$ is as just defined with previous (method H) or subsequent (method A1) introduction of a group R.

The starting material for method (b) may be prepared by one of the following methods.

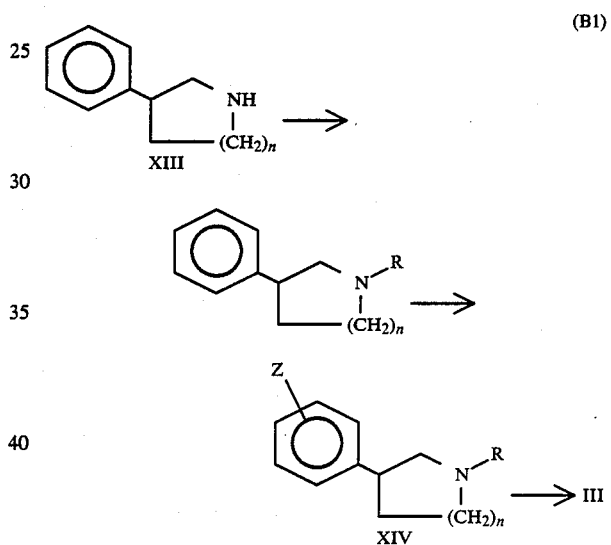
(B1)

In a compound of formula XIII a group R may be introduced as previously described whereupon the compound is treated with Cl$_2$ or H$_2$SO$_4$ to the formation of an isomeric mixture XIV, from which the compound III wherein Z is Cl or SO$_3$H is obtained by chromatographic separation.

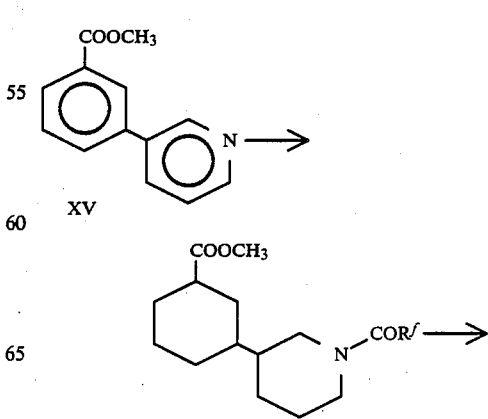

-continued

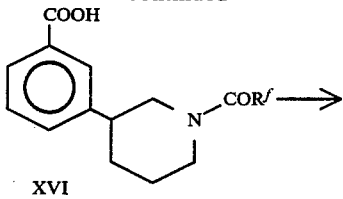
XVI

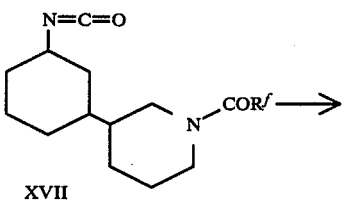
XVII

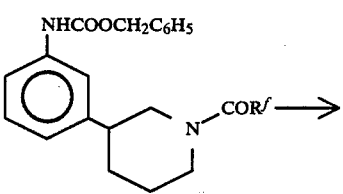
XVIII

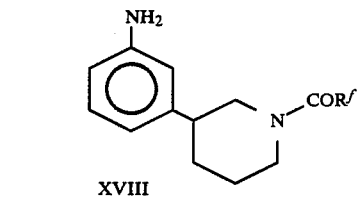
XVIII

The compound of formula XV is hydrogenated under acidic conditions in the presence of PtO₂ to give a phenylpiperidine which is N-acylated with an appropriate carboxylic acid chloride R$^f$COCl wherein R$^f$ is an alkyl group having 1–4 carbon atoms or an ethoxy group, in the presence of a base such as triethylamine, giving an amide, which is subjected to mild acid or basic hydrolysis of the ester function giving a compound XVI. Said compound XVI is treated with ClCOOC₂H₅ and triethylamine and then with sodium azide giving a carboxylic acid azide which on heating gives the isocyanate XVII. The isocyanate is treated with an excess of boiling benzyl alcohol giving a carbamate which is then hydrogenated in the presence of Pd/C to give a compound XVIII. A compound of formula III wherein Z is NH₂ and n is 2 is then formed by subjecting the amide group of compound XVIII to splitting with an aqueous acid or base when an N-unsubstituted compound is desired, to reduction with e.g., LiAlH₄ when R= an alkyl group having 2–5 carbon atoms is desired. When R=CH₃ is desired a compound XVIII wherein R$^f$ is an ethoxy group may be treated with LiAlH₄.

The starting materials for method (e) may be prepared by one of the following methods (E1)

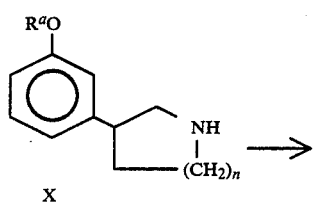
X

-continued

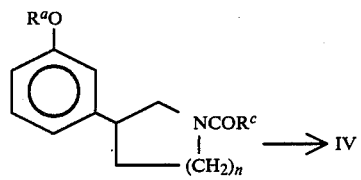
XIX

A compound of formula XIX may be formed by N-acylation of a corresponding compound of formula X, preparable according to A1 above, with an acid chloride R$^c$COCl in the presence of a base. The ether function of compound XIX is then cleaved with BBr₃ to the formation of a compound of formula IV wherein M¹ and M² are both —CH₂— and R$^d$ is H. If desired the hydroxy group may then be acylated with an acyl chloride to form a compound of formula IV wherein R$^d$ is R¹CO, or alkylated with an allyl or benzyl halide to form a compound of formula IV wherein R$^d$ is allyl or benzyl.

(E2)

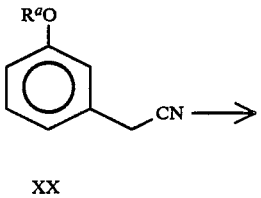
XX

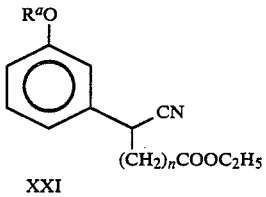
XXI

A compound of formula XX wherein R² is alkyl having 1–5 carbon atoms is reacted with I(CH₂)$_n$COOC₂H₅, or alternatively when n=2 is desired with CH₂=CH—COOC₂H₅, in the presence of a base to the formation of a compound of formula XXI. When n=1 is desired compound XXI may be prepared by the following route.

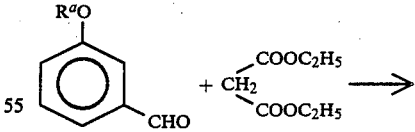
XXII

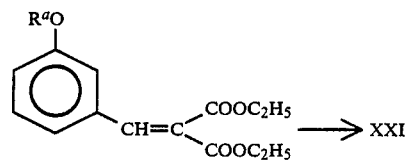

The compound obtained by reaction of the alkoxybenzaldehyde with diethylmalonate is reacted with KCN in ethanol to the formation of a compound XXI wherein n is 1.

The compound XXI obtained by one of said routes is then converted into a compound of formula IV along the following route.

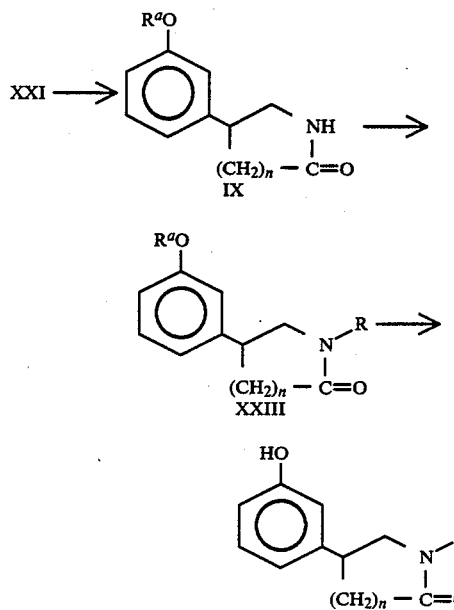

Compound XXI is treated with hydrogen in the presence of a catalyst such as Raney nickel to the obtention of compound XI, in which a substituent is introduced at the nitrogen atom, if required in the end compound, by means of a halide RX. The ether function is then cleaved with $BBr_3$ giving a compound IV wherein $R^d$ is H and $M^1$ is —$CH_2$— and $M^2$ is $$\diagdown C=O$$

and, if required in compound IV, the hydroxy group is acylated with an acyl chloride $R^1COCl$ in the presence of a base, or alkylated with an allyl or benzyl halide to form a compound of formula IV wherein $R^d$ is allyl or benzyl.

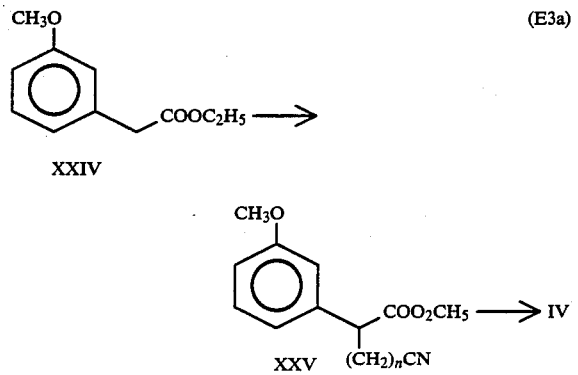

A compound of formula XXIV is reacted with $I(CH_2)_n CN$, or alternatively when n=2 is desired with $CH_2$=CH—CN, in the presence of a base, to the formation of a compound XXV. The subsequent route for preparation of the compound IV wherein $M^1$ is $$\diagdown C=O$$

and $M^2$ is —$CH_2$— is completely analogous to the route XXI to IV described above.

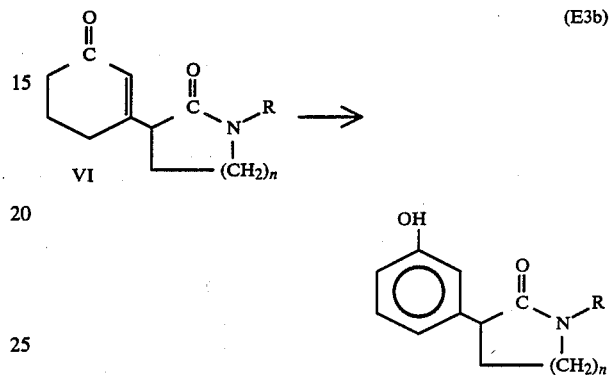

A compound of formula IV wherein $M^1$ is $$\diagdown C=O,$$

$M^2$ is —$CH_2$—, $M^3$ is R, $R^d$ is H and n is 1 or 2 may be prepared by oxidation of a compound of formula VI above e.g. with $Br_2$.

A compound of formula XXI is heated with an aqueous acid to the formation of a dicarboxylic acid XXVI, which is then reacted with acetic acid anhydride. Heating of the resulting cyclic anhydride with an amine R—$NH_2$ yields an imide XXVII, in which the ether function is cleaved with BBr₃ giving a compound IV wherein $R^d$ is H and $M^1$ and $M^2$ are both

and, if required, the hydroxy group is acylated to the formation of compound IV, wherein $R^d$ is $R^1CO$, or alkylated with an allyl or benzyl halide to form a compound of formula IV wherein $R^d$ is allyl or benzyl.

The starting material for method (f) may be prepared by the following method.

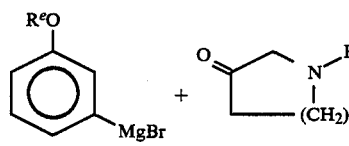

A Grignard reaction with compounds XXVIII and XXIX produces compound V. The compound XXIX may be prepared by reacting a compound of the formula

with an alkyl bromide RBr in the presence of a base such as $K_2CO_3$ when an alkyl group R is required.

Starting material for method (h) may be prepared by the following method.

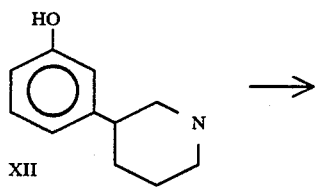

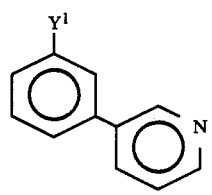

When a group $Y^1$ other than hydroxy is required, such a group is introduced by reaction of a compound XII with an appropriate acyl, carbamoyl, benzyl or allyl chloride in the presence of a base. The pyridyl nitrogen is then reacted with a hydrogen halide or alkyl halide $RX^1 (X^1=Br$ or I) to the formation of an ion VII.

Starting materials for method (i) may be prepared by one of the following methods.

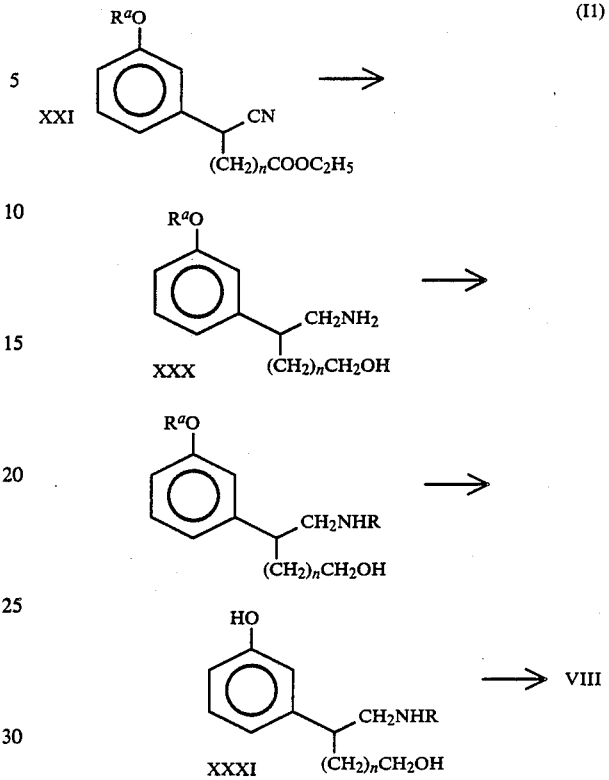

A compound of formula XXI, obtainable according to method (E2), is reduced with LiAlH₄ to the formation of compound XXX, which is N-substituted with a halide $RX^1$, wherein $X^1$ is a halogen, in the presence of a base. In the compound obtained the ether function is cleaved with aqueous HBr to the formation of a compound XXXI. A leaving group X is then introduced to the formation of compound VIII, wherein $Z^1$ is NHR and $Z^2$ is X, by reaction with thionyl chloride, whereby X=Cl is obtained, or with an acid HX.

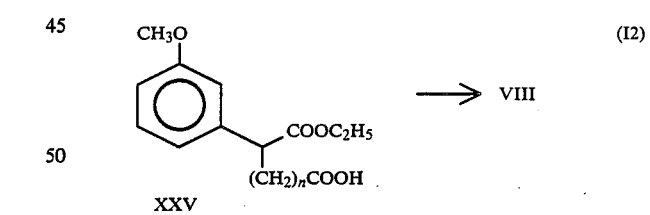

A compound of formula XXV, obtainable according to method (E3), is converted into a compound of formula VIII, wherein $Z^1$ is X and $Z^2$ is NHR, in a manner analogous to the conversion XXI to VIII under (I1) above.

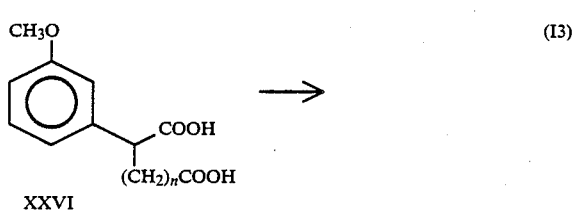

-continued

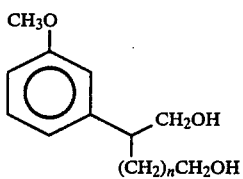

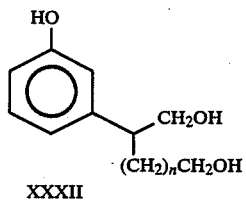 → VIII

XXXII

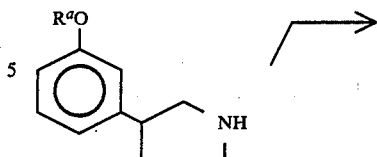
8

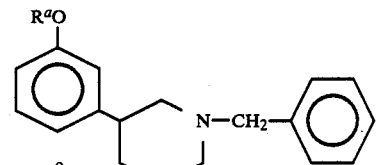
9

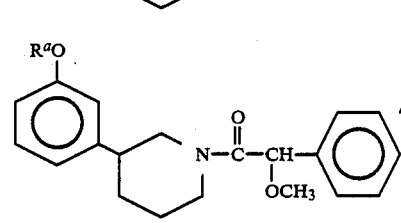
10

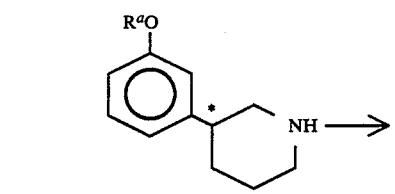
11

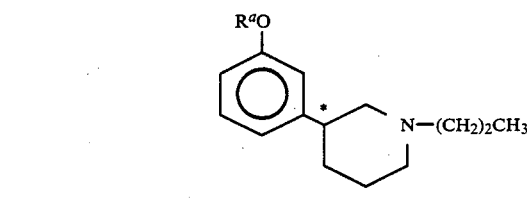
12

A compound of formula XXVI, obtainable according to method (E4), is reduced with LiAlH₄. In the resulting compound the ether function is cleaved with aqueous HBr to the formation of a compound of formula XXXII. In compound XXXII two leaving groups X are introduced to the formation of a compound VIII, wherein $Z^1$ and $Z^2$ are each X, by reaction with thionyl chloride, whereby X=Cl is obtained, or with an acid HX.

INTERMEDIATES

Some of the intermediates or starting materials mentioned above and the preparation thereof are known. However, certain intermediates or starting materials are novel and constitute a further aspect of the invention. Thus in one aspect the invention is related to novel compounds of the formula

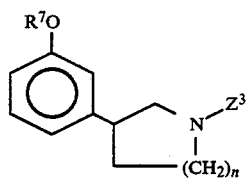

wherein $Z^3$ is R or $R^6CO$ wherein $R^6$ is an alkyl or alkoxy group containing 1–4 carbon atoms or an alkenyl group with 2–4 carbon atoms, $R^7$ is an alkyl group with 1–5 carbon atoms, an allyl or benzyl group and n is 1 or 2 provided that $Z^3$ is other than methyl and ethyl when n is 2 and $R^7$ is CH₃, as well as to acid addition salts (where possible) of said compounds, and to the methods for preparing said compounds or salts.

Starting materials for the methods of preparation described in Section II above may be obtained by several methods known in the art in particular in EP-A1-0 030 526, and/or described below.

The starting material for method (j) according to formula 2 above may be prepared by the following method:

A compound of formula 8 (racemic mixture) wherein $R^a$ is an alkyl group having 1–5 carbon atoms or an acyl group having 2–6 carbon atoms is resolved either by first conversion into the N-benzyl analogue 9 followed by recrystallization of the (+)-tartaric acid salt and debenzylation by hydrogenation, or (when $R^a$ is alkyl) by first conversion into the (−)-O-methylmandelic acid amide (10) followed by chromatographic separation of the two diastereomers and cleavage by KOBuᵗ in tetrahydrofuran with traces of water. The enantiomer with the desired absolute configuration 11 is then alkylated by propionylation followed by LiAlH₄ reduction to the formation of compound 2 having the appropriate absolute configuration at the asymmetric carbon(*) atom.

The starting material for method (k) may be prepared by the following method:

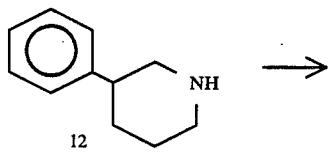

12

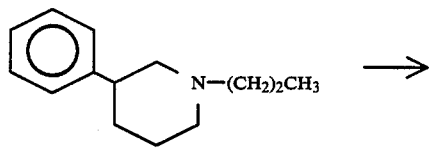

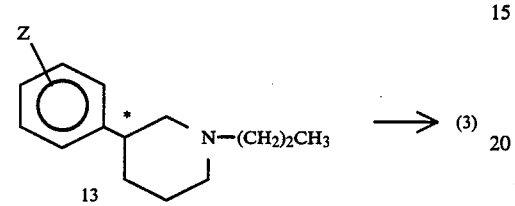                                         (3)

13

In a compound of formula 12 a group n—$C_3H_7$ may be introduced as previously described with previous (method j) or subsequent (method q) resolution into the desired enantiomer whereupon the compound is treated with $Cl_2$, $H_2SO_4$ or $HNO_3$ followed by reduction to the formation of an isomeric mixture 8, from which the compound 3 wherein Z is Cl, $SO_3H$ or $NH_2$ is obtained by chromatographic separation.

(D) The starting materials for method (m) may be prepared according to method (j) above.

A starting material for method (n) may be prepared by the following method

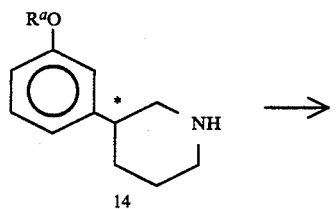

14

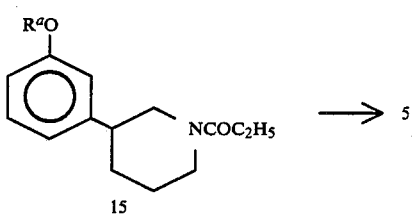

15

A compound of formula 15 may be formed by N-acylation of a corresponding compound of formula 14, preparable according to j above, with $C_2H_5COCl$ in the presence of a base. The ether function of compound 15 is then cleaved with $BBr_3$ to the formation of a compound of formula 5 wherein $M^1$ and $M^2$ are both —$CH_2$— and $R^d$ is H. If desired the hydroxy group may then be acylated with an acyl chloride to form a compound of formula 5 wherein $R^d$ is $R^1CO$, or alkylated with an allyl or benzyl halide to form a compound of formula 5 wherein $R^d$ is allyl or benzyl.

The starting material for method (o) may be prepared by the following method.

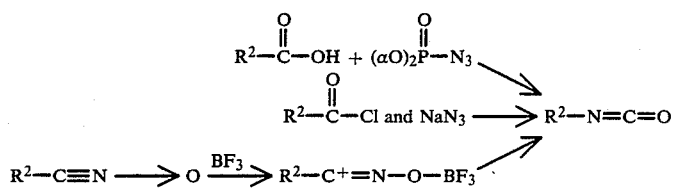

A Grignard reaction with compounds 16 and 17 followed by elimination of the hydroxy-group produces compound 6.

Starting materials for method (p) may be prepared by enantiomeric separation of the corresponding racemate or a precursor thereof.

Thus, the compound of formula bII and the compound of formula bV above are obtainable as described in EP-Al-0030526. To obtain said compound in pure enantiomeric form enantiomer separation is carried out on the racemic compound or a precursor thereof as further described in European Patent Application No. 83850084.1.

The isocyanate employed by method (r) may be formed in situ by one of the reactions $$R^2-\overset{O}{\underset{\|}{C}}-OH + (\alpha O)_2\overset{O}{\underset{\|}{P}}-N_3$$

$$R^2-\overset{O}{\underset{\|}{C}}-Cl \text{ and } NaN_3 \longrightarrow R^2-N=C=O$$

$$R^2-C\equiv N \longrightarrow O \xrightarrow{BF_3} R^2-C^+=N-O-BF_3^-$$

whereby $\phi$ represents phenyl.

PHARMACEUTICAL PREPARATIONS

Pharmaceutical preparations of the compounds of the invention constitute a further aspect of the invention. For such preparations reference is made to pages 23 to 25 of EP-A10030526 which is incorporated by reference herein.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, e.g. the hydrochloride, lactate, acetate, sulfamate, and the like, in association with a pharmaceutically acceptable carrier.

Accordingly, terms relating to the novel compounds of this invention, whether generically or specifically, are intended to include both the free amine base and the acid addition salts of the free base, unless the context in which such terms are used, e.g. in the specific examples, would be inconsistent with the broad concept. The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparation intended for injection and between 0.2 and 50% by weight for preparations suitable for oral administration.

Pharmaceutical preparations containing a compound of the invention in a solid form of dosage units for oral application may preferably contain between 2 and 50% by weight of the active substance; in such preparations the selected compound may be mixed with a solid fine grain carrier, e.g. lactose, saccharose, sorbitol, mannitol, starches such as potato starch, corn starch or amylopectin, cellulose derivatives, or gelatin and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatin, talcum, titanium dioxide, and the like. Alternatively the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and, for example, glycerol, or similar closed capsules, the active substance may be admixed with a vegetable oil. Hard gelatin capsules may contain granulates of the active substance in combination with solid, fine grain carriers such as lactose, saccharose, sorbitol, mannitol, starches (e.g. potato starch, corn starch or amylopectin), cellulose derivatives or gelatin.

Liquid preparations for oral application may be in the form of syrups or suspensions, for example, solutions containing from about 0.2% to about 20% by weight of the active substance herein described, the balance being sugar and a mixture of ethanol, water, glycerol and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

In therapeutical treatment the suitable daily doses of the compounds of the invention are 200–10,000 mg for oral application, preferentially 1,000–6,000 mg, and 1–1,000 mg for parenteral application, preferentially 50–500 mg.

WORKING EXAMPLES

The following examples will further illustrate the invention.

Preparation of intermediates

Example I1.

N-Butyl-3-(3-methoxyphenyl)piperidine hydrochloride (Method A1 and e)

Butyryl chloride (2.0 g, 0.019 mol) in dry toluene (5 ml) was slowly added to a solution of 3-methoxyphenyl-piperidine (2.45 g, 0.013 mol) and triethylamine (1.92 g, 0.013 mol) in dry toluene at 5°. The mixture was stirred at room temperature for 30 min., whereupon the triethylammonium chloride formed was filtered off and the solvent evaporated. The crude N-butyryl-3-(3-methoxyphenyl)piperidine (2.82 g) dissolved in dry tetrahydrofuran (30 ml) was added to a suspension of LiAlH$_4$ (2.0 g) in dry tetrahydrofuran (30 ml) under nitrogen. After reflux for 3 h the mixture was hydrolysed, the precipitate filtered off and the solvent evaporated. The residue dissolved in light petroleum was passed through an alumina column. (Alternatively the residue could be distilled in vacuo.) The product was precipitated as the hydrochloride and recrystallized from ethanol/ether yielding the pure product (3.6 g, 88%) mp 130-1° C.

Example I2.

N-Propyl-3-(3-methoxyphenyl)pyrrolidine (Method A1 and e)

3-(3-methoxyphenyl)pyrrolidine (8.86 g, 0.050 mol) and triethylamine (5.57 g, 0.055 mol) was dissolved in 500 ml of dry ether. The solution was cooled to 0° C and propionyl chloride (5.09 g, 0.055 mol) was added dropwise with stirring. The reaction mixture was then allowed to acquire ambient temperature, whereafter it was refluxed for 30 minutes. Triethylamine hydrochloride was filtered off, and the filtrate was evaporated leaving 11.7 g (100%) of crude N-propionyl-3-(3-methoxyphenyl)pyrrolidone, which was used in the next reaction step without further purification. The crude amide (11.7 g, 0.050 mol) was reduced with LiAlH$_4$ (2.85 g, 0.075 mol) in refluxing ether (200 ml) for 24 hours. Workup of the reaction mixture afforded 10 g of product, which upon distillation in vacuo yielded 9.1 g (83%) of N-propyl-3-(3-methoxyphenyl)-pyrrolidine b.p. 85–86° C/0.1 mm Hg. MS: m/e 219 (M+, 12%) 190 (M—C$_2$H$_5$, 100%).

Example I3.

N-Pentyl-3-(3-methoxyphenyl)piperidine (Method A1 and d)

To a solution of 3-(3-methoxyphenyl)piperidine (3.92 g, 0.02 mol) in CH$_3$CN (100 ml), solid K$_2$CO$_3$ (5 g) was added and then the mixture was refluxed. A solution of pentyliodide (4.5 g, 0.021 mol) in CH$_3$CN (10 ml) was added dropwise under 30 min. and then the mixture was refluxed for an additional 30 min. The solid was filtered off from the cooled mixture, and the solvent evaporated giving an oil which was chromatographed on a silica gel column with methanol as eluant. Yield 1.3 g (25%) of pure N-pentyl-3-(3-methoxyphenyl)piperidine (NMR) as an oil.

Example I4.

N-Propyl-3-(3-methoxyphenyl) piperidine hydrochloride (Method A1 and d)

NaBH$_4$ (6.08 g, 0.16 mol) was added portionwise under stirring to a solution of propionic acid (38 g, 0.51 mol) in dry benzene (150 ml). The temperature was kept below 15° C. for 2 h and then 3-(3-methoxyphenyl)-piperidine (6.1 g, 0.032 mol) dissolved in dry benzene (100 ml) was added and the mixture was refluxed for 3 h. The reaction mixture was allowed to reach room temperature and was then extracted with 2.5 M NaOH (200 ml). The aqueous phase was extracted with benzene, all the benzene phases mixed, dried ($Na_2SO_4$) and the solvent evaporated giving an oily residue (6.6 g). The product was precipitated as hydrochloride and recrystallized from methanol/isopropyl ether yielding the pure product (6.2 g, 72%), mp. 191° C.

Example I6.

N-Propyl-3-(3-methoxyphenyl)piperidine hydrobromide (Method A2 and h)

3-(3-pyridinyl)methoxybenzene (3.0 g, 0.016 mol) and propyl bromide (2.0 g) was dissolved in dry acetone (50 ml) and allowed to react at 110° C. in a high pressure steel vessel. After 20 h the reaction was interrupted and the solvent was evaporated. The residual quartenary N-propyl-3-(3-methoxyphenyl) pyridinium bromide was hydrogenated ($PtO_2$) in methanol at r.t. and 760 mmHg. The $H_2$-uptake ceased after 24 h. The catalyst was filtered off and the solvent evaporated. The hydrobromide was recrystallized from ethanol/ether giving 2.63 g (70%) of the pure product, mp. 155–156° C.

Example I7.

3-(3-Pyridinyl)methoxybenzene (Method A2)

This substance was prepared by a dichlorobis-(triphenylphosphine)nickel (II) catalyzed reaction between 3-methoxyphenylmagnesium bromide (from 50 g of 3-bromo-anisole and 5.9 g of Mg in THF) and 31.8 g of 3-bromopyridine. Yield 23.1 g (62%), bp. 102° /0.15 mmHg, mp. (HCl) 187.5–9° C.

Example I8.

3-(3-Methoxyphenyl)piperidine hydrochloride (Method A2 and h)

To a solution of 3-(3-pyridinyl)methoxybenzene (22.0 g, 0.099 mol) in methanol (250 ml), $PtO_2$ (2 g) and conc. HCl (30 ml) were added and the mixture was hydrogenated at 0.34 MPa in a Parr apparatus. After complete hydrogenation, the catalyst was filtered off. Most of the solvent was evaporated, the residue was made alkaline with 1M NaOH and extracted with ether. The ether-phase was dried ($Na_2SO_4$) and the solvent evaporated giving 18 g of the amine product. The hydrochloride was made and then recrystallized from ethanol/ether yielding 20.9 g (93%), mp. 137–138.5° C.

Example I9.

N-n-Propyl-3-(3-aminophenyl)piperidine hydrochloride (Method B2)

3-(3-Methylphenyl)-pyridine 3-(3-methylphenyl)-pyridine was prepared from 81.5 g (0.52 mol) 3-bromopyridine and 120 g (0.70 mol) 3-bromo-toluene as described for the preparation of 3-(3-methoxyphenyl)-pyridine. (Example I7.) B.p. 87° /0.05 mmHg. Yield 61.7 g (69%).

Methyl-3-(3-oyridyl)-benzoate

A mixture of 3-(3-methylphenyl)-pyridine (30 g, 0.177 mol), potassium permanganate (67.5 g, 0.427 mol) and water (825 ml) was refluxed overnight with stirring. The hot mixture was filtered, acidified (conc. HCl) and evaporated in vacuo. After drying in the air the solid was dissolved in HCl-saturated methanol (2500 ml), the resulting solution was refluxed for 24 hours. The methanol was evaporated and the residue was made alkaline with saturated potassium carbonate solution. Extraction with ether followed by drying ($K_2CO_3$) and evaporation of the ether gave an oil which was distilled in vacuo. The fraction distilling from 90° C. to 135° C. at 0.2 mm was then filtered through a $SiO_2$-column with ether as eluant. Evaporation of the ether gave the pure product (21 g, 55%) as a solid.

The hydrochloride was prepared by dissolving the amino-ester in ether followed by addition of HCl-saturated ether. The salt was recrystallized from methanol/ether, mp. 208°–209° C.

3-(1-Propionylpiperidin-3-yl)-benzoic acid

A solution of the HCl-salt of methyl-3-(3-pyridyl)-benzoate (5.54 g, 0.022 mol) in methanol was hydrogenated (atm. pressure) at r.t. using $PtO_2$ as catalyst. After filtration and evaporation the residue was partitioned between a saturated potassium-carbonate solution and ether. The ether layer was dried ($K_2CO_3$), cooled and treated with triethylamine (2.23 g. 0.022 mol) and propionylchloride (2.05 g), 0.033 mol). Stirring at r.t. for one hour followed by filtration and evaporation gave an oil which was eluated twice through an $Al_2O_3$-column with ether. Evaporation of the ether gave 4.8 g of pure methyl-3-(1-propionylpiperdin-3-yl)benzoate as an oil, which could not be crystallized.

A mixture of methyl-3-(1-propionylpiperidin-3-yl)benzoate (4.8 g, 0.17 mol), sodium hydroxide pellets (5 g), methanol (80 ml) and water (20 ml) was stirred until TLC indicated that no starting material remained (4 hours). The methanol was evaporated and the alkaline water layer was washed with ether, acidified with hydrochloride acid and extracted with chloroform. Evaporation gave the product (4.0 g, 69% yield from methyl-3-(3-pyridyl)-benzoate) as an oil which crystallized after several weeks on standing. (Mp. 125°–126° C.)

N-propyl-3-(3-Aminophenyl)-piperidine hydrochloride

To a cooled (−10° C.) solution of 3-(1-propionyl-piperidin-3-yl)benzoic acid (9.75 g, 0.036 mol) and triethylamine (3.56 g, 0.033 mol) in acetone (115 ml) ethyl chloroformate (4.34 g, 0.040 mol), was slowly added. After stirring at −10° C. for one and a half hour, a solution of sodium azide (3 g, 0.046 mol) in water (10 ml) was added dropwise, and the mixture was stirred at −10° C. for one hour more. The reaction mixture was poured into icewater and extracted with toluene. The toluene extract was dried ($MgSO_4$) and heated until a small sample run on IR indicated that the reaction (the conversion of the acyl azide to the isocyanate) was complete. Evaporation of the toluene gave the isocyanate as an oil.

The isocyanate was boiled with benzyl alcohol (20 ml) until the reaction was complete (IR; 24 hours). Evaporation of unreacted benzylalcohol gave an oil (1.5 g) which was dissolved in methanol and hydrogenated at r.t. and atmospheric pressure with 10% Pd/C as catalyst. Filtration and evaporation gave an oil which was further reacted with $LiAlH_4$ (1.0 g, 0.026 mol) in tetrahydrofuran. Refluxing for 3 h followed by hydrolysis of the reaction mixture, filtration and evaporation of the solvent gave the crude N-n-propyl-3-(3-aminophenyl)piperidine which was converted to its dihydrochloride by dissolving the base in methanol and saturating the solution with HCl. Evaporation of the methanol gave the salt as an oil. Yield: 0.40 g (4%, calculated on 3-(1-propionylpiperidin-3-yl)benzoic acid). A sample of the oil was reconverted to the base and dissolved in CDCl$_3$ for NMR (see table).

Preparation of intermediates

Example I10.

(+)-3-(3-Methoxyphenyl)piperidine hydrochloride (Method j).

(+-Dibenzoyl-D-tartaric acid (28.2 g, 0.075 mol) in hot methanol (350 ml) was added to N-benzyl-3-(3-methoxyphenyl) piperidine (21.1 g, 0.075 mol) in hot methanol (100 ml). After two days the salt that separated was recrystallized three times from methanol. The collected salt (8.3 g) was treated with 1M NaOH (250 ml) and the free amine was extracted with ether (3×150 ml). The combined ether layers were dried (K$_2$CO$_3$) and the solvent evaporated. The residual amine was then passed through a short alumina column with ether as eluant and then converted to the hydrochloride. One recrystallization from methanol-ether gave (−)-N-benzyl-3-(3-methoxyphenyl)-piperidine hydrochloride (3.8 g), m.p. 164°–165° C; [α]$^{22}$D −43.1° (C 2.1, CH$_3$OH).

(−)-N-benzyl-3-(3-methoxyphenyl)piperidine hydrochloride (3.8 g, 0.0120 mol) was dissolved in ethanol (80 ml), 10% Pd/C was added and the mixture was hydrogenated at room temperature and atmospheric pressure (28 h). The catalyst was removed (Celite) by filtration, the solvent was evaporated off and the crystalline residue was recrystallized from methanol-ether giving the desired (+)-3-(3-methoxyphenyl)-piperidine hydrochloride (2.54 g, 30% total yield of the maximal theoretical) m.p. 175.5°–177° C.; [α]$^{22}$ D+10.1° (C 2.1, CH$_3$OH).

Example I11.

(+)-3-(3-Methoxyphenyl)piperidine hydrochloride (Method j).

R−(−)-α-Methoxyphenylacetic acid (11.0 g, 0.066 mol) and SOCl$_2$ (85 ml) was mixed under ice-cooling and the mixture was stirred at 20° for 2 h. Excess of SOCl$_2$ was evaporated off (at 20° ) and the residual acid chloride oil was dissolved in CH$_2$Cl$_2$. The solution was added at 20° to a stirred mixture of 3-(3-methoxyphenyl)piperidine hydrochloride (15.1 g, 0.066 mol), CH$_2$Cl$_2$(280 ml) and 2.5% aqueous NaOH (560 ml). After 10 minutes stirring the phases were separated and the organic phase was washed once with water and dried (Na$_2$SO$_4$). Filtration and evaporation of the solvent gave 1-(R-α-methoxyphenylacetyl)-3-(3-methoxyphenyl) piperidine as a crude oil (21.8 g).

The crude oil of 1-(R-α-methoxyphenylacetyl)-3-(3-methoxyphenyl)-piperidine (21.8 g) was chromatographed on a SiO$_2$ column (600 g SiO$_2$) with light petroleum-ether (starting with 50:50 mixture and successively increasing the ether content to 100%) as eluant. The fractions containing that one of the two diastereomers, which is eluated first, in nearly pure form were combined and the solvent evaporated off giving the desired diastereomeric amide as an oil (7.7 g, 0.023 mmol) (containing 0.5% of the other diastereomer according to HPLC). This was dissolved in dry tetrahydrofuran (400 ml) and potassium-tert-butoxide (16.1 g, 0.144 mol) and water (1.33 g, 0.074 mol) was added under stirring at room temperature. The mixture was stirred at this temperature over night and then the mixture was partitioned between ether and water. After drying (Na$_2$SO$_4$) of the organic phase excess of HCl-saturated ethanol was added and the solvent was evaporated off. The residue was redissolved twice in absolute ethanol and the solvent evaporated, giving a crystalline residue. Recrystallization from ethanol-ether gave the desired (+)-3-(3-methoxyphenyl)piperidine hydrochloride (4,0 g, 53% total yield of the maximal theoretical), m.p. 175.5°–177° C.; [α]$^{22}$D=+10.1° (C 2.1, CH$_3$OH).

Example I12.

(−)-3-(3-Methoxyphenyl)-N-n-propylpiperidine hydrochloride (Method j, and n)

(+)-3-(3-Methoxyphenyl)piperidine hydrochloride (1.5 g, 0.0066 mol) was treated with 2 N NaOH (50 ml) and the free amine was extracted with ether. After drying (K$_2$CO$_3$3), filtering and evaporation the residual free amine oil (1.2 g) was dissolved in dry ether (50 ml) and the triethylamine (1.4 ml, 0.0010 mol) was added. Then propionyl chloride (0.87 ml, 0.0010 mol) dissolved in dry ether (5 ml) was slowly added at 0° under stirring, and the mixture was stirred at room temperature for 30 min. The precipitate was filtered off and the solvent was evaporated giving an oily residue. This residue was dissolved in dry tetrahydrofuran (50 ml) and added to a suspension of LiAlH$_4$ (0.75 g, 0.0020 mol) in dry tetrahydrofuran (75 ml) under N$_2$. After refluxing for 4 h. the mixture was hydrolysed, the precipitate was filtered off and the solvent was evaporated. The residue was dissolved in ether and passed through an alumina column with ether as eluant. Addition of HCl saturated ethanol, evaporation of the solvent and recrystallization gave (−)-3-(methoxyphenyl)-N-n-propyloiperidine hydrochloride (1.48 g. 83%), 200,5–202° C.; [α]$^{22}$D −6.7 (C 2.1, CH$_3$OH).

Example I13.

(−)-3-(3-methoxyphenyl)-N-n-propyl piperidine hydrochloride (Method j and m).

NaBH$_4$ (0.61 g, 0.016 mol) was added portionwise under stirring to a solution of propionic acid (3.6 g, 0.051 mol) in dry benzene (15 ml). The temperature was kept below 15° C. for 2 h and then (+)-3-(3-methoxyohenyl)-piperidine (0.61 g, 0.0032 mol) dissolved in dry benzene (10 ml) was added and the mixture was refluxed for 3 h. The reaction mixture was allowed to reach room temperature and was then extracted with 2.5 M NaOH (20 ml). The aqueous phase was extracted with benzene, all the benzene phases mixed, dried (Na$_2$SO$_4$) and the solvent evaporated giving an oily residue. The product was precipitated as hydrochloride and recrystallized from methanol/ether, yielding the pure product (0.60 g, 73%), mp. 200°–202° C.

Preparation of end compounds

Example E1.

N-n-propyl-3-(3-hydroxyphenyl)piperidine hydrobromide (Method a)

N-Propyl-3-(3-methoxyphenyl)piperidine hydrochloride (7.0 g, 0.026 mol) was suspended in 48% HBr (200 ml). The mixture was refluxed under nitrogen for 3 h. The hydrobromic acid was evaporated and the residue was recrystallized from ethanol/ether, yielding the pure product (6.7 g, 86%) mp. 146°–7.5° C.

Example E2.

N-pentyl-3-(3-hydroxyphenyl)piperidine hydrochloride (Method a)

N-pentyl-3-(3-methoxyphenyl)piperidine (1.3 g, 0.005 mol) in $CH_2Cl_2$ (20 ml) was cooled with dry ice and $BBr_3$ (1.6 g, 0.006 mol) was added dropwise. The mixture was then held at −78° C. for 1 h and then allowed to reach r.t. overnight. The solution was made alkaline with aqueous $Na_2CO_3$, extracted with $CH_2Cl_2$ and the organic phase dried with $Na_2SO_4$. Evaporation of the solvent afforded an oily residue which was treated with HCl-saturated ethanol (5 ml). After evaporation of solvent, purification by extractions and recrystallization (ethanol/ether), the desired product (0.40 g, 29%) was obtained, mp. 70°-80° C.

Example E3.

N-n-Propyl-3-(3-acetoxyphenyl)piperidine hydrochloride (Method c)

N-n-propyl-3-(3-hydroxyphenyl)piperidine (0.8 g, 0.0037 mol) was dissolved in acetic anhydride (20 ml). Triethylamine (1 ml) was added and the solution was refluxed for 1.5 h, ethanol (50 ml) was added and the volatiles were evaporated giving a residual oil. The residue was partitioned between ether and water. Separation of the two phases and evaporation of the ether gave an oily residue (700 mg). This was dissolved in dry ether (100 ml) and HCl-saturated ether was added giving the desired compound as a crystalline precipitate, which was filtered off and recrystallized from methanol/isopropyl ether. Yield 0.60 g (55%), mp. 173°-175° C.

Example E4.

N-n-Propyl-3-(3-benzoyloxyphenyl)piperidine hydrochloride (Method c).

N-n-Propyl-3-(3-hydroxyphenyl)piperidine (0.5 g, 0.0023 mol) was dissolved in $CH_2Cl_2$. Triethylamine (1 ml) and benzoyl chloride (0.5 ml, 0.004 mol) was added and the mixture was stirred at r.t. for 48 h. The solvent was evaporated and the residue was partitioned between ether and water. The ether phase was dried ($Na_2SO_4$) and the solvent evaporated giving an oily residue which was eluated through a short silica gel column with methanol as eluant. Evaporation of the solvent gave an oily residue (300 mg). The oil was dissolved in ether and HCl-saturated ether was added. Filtration and drying gave the desired compound in a crystalline form. Yield 13%, mp. 170° C.

Example E5.

2-[3-(3-Hydroxyphenyl)-piperidino]ethanol hydrochloride (Method d)

Ethylenoxide (0.36 ml, 7.0 mmol) was added to a stirred solution of 3-(3-hydroxyphenyl)piperidine (1.0 g, 5.6 mmol) in methanol (150 ml), maintaining the temperature at −30° C., whereafter the reaction mixture was allowed to reach room temperature. (The reaction was followed by TLC). More ethylenoxide (0.5 ml, 9.8 mmol) was added in portions until the reaction was complete (two weeks). An excess of ethereal hydrogen chloride was added and the solvent was evaporated. The oily residue was passed through a silica column with 10% methanol in chloroform. After evaporation the hydrochloride was recrystallized from ethanol/ether to yield 0.6 g (41%) of 2-[3-(3-hydroxyphenyl)-piperidino]ethanol hydrochloride, m.p. 116.5°-120° C.

Example E6.

N-n-Propyl-3-(3-hydroxyohenyl)piperidine hydrochloride (Method b)

To a solution of N-n-Propyl-3-(3-aminophenyl)-piperidine (0.74 g, 0.0034 mol) in 6M $H^2SO_4$ (2 ml) $NaNO_2$ (0.23 g, 0.0034 mol) dissolved in water (0.6 ml) was added dropwise at 5° C. and then the mixture was stirred at 5° C. for 1 h. The resulting mixture was added dropwise to refluxing 10% $H_2SO_4$ (3.5 ml) and the reflux was continued for 5 min. Cooling alkalising ($Na_2CO_3$), extraction with ether, drying and evaporation of the organic phase gave the desired product as a free base. Conversion to the hydrochloride followed by recrystallization gave 0.22 g (25%) of N-n-propyl-3-(3-hydroxyphenyl)piperidine hydrochloride, mp. 143.5°-146° C.

Example E7.

N-n-Propyl-3-(3-allyloxyphenyl)piperidine hydrochloride (Method e)

A solution of N-n-propionyl-3-(3-allyloxyphenyl)-piperidine (0.35 g, 0.0013 mol) in dried ether (25 ml) was dropped to a suspension of $LiAlH_4$ (0.35 g) in dried ether under nitrogen and stirring, and the mixture was refluxed for 30 min. $H_2O$ (0.35 ml), 15% NaOH (0.35 ml) and $H_2O$ (1 ml) were added and the precipitated crystals were filtered off and washed with ether. The solution was dried with $Na_2SO_9$. Evaporation to dryness gave an oily residue which was dissolved in ether. Addition of HCl-saturated ether resulted in precipitation of white crystals. The crystals were centrifugated and treated with light petroleum, centrifugated and dried. Yield 0.185 g (49%).

Example E8.

N-n-Propyl-3-(3-benzyloxyphenyl)piperidine hydrochloride (Method c)

A mixture of N-n-propyl-3-(3-hydroxyphenyl)piperidine hydrobromide (1.0 g. 0.0033 mol), potassium t-butoxide (1.0 g, 0.009 mol) and benzylchloride (1.0 g, 0.009 mol) in t-butanol (25 ml) was refluxed for 1 h. Water was added and the mixture extracted with ether. The organic phase was dried with $Na_2SO_4$ and evaporated to dryness giving a pale yellow oily residue. The residue was chromatographed through a silica gel column with methanol as eluant. The pertinent fractions were collected and evaporated to dryness. The oily residue was dissolved in ether and HCl-saturated ether was added, giving white crystals. Evaporation and treatment of the residue with acetone gave 0.60 g (52%) of the desired product as white crystals, mp. 171° C.

Example E9.

N-n-Propyl-3[3-(phenylcarbamoyloxy)phenyl]-piperidine hydrochloride (Method c)

A mixture of N-n-propyl-3-(3-hydroxyphenyl)piperidine hydrobromide (0.76 g, 0.0025 mol), phenylisocyanate (5.45 g, 0.046 mol), triethylamine (0.5 g, 0.049 mol) and methylene chloride (2 ml) was stirred at r.t. for 18 h. The mixture was partitioned between water and ether. The ether phase was dried and evaporated giving a partly crystalline residue. The residue was dissolved in methanol and chromatographed on a silica gel column (200 g, SiO$_2$) with methanol as eluant. The fractions which according to GLC contained the desired product in pure form were continued and the solvent evaporated. The residue was dissolved in ether and treated with HCl-saturated ether giving a crystalline precipitate. Filtration and washing gave 0.18 g (20%) of the desired hydrochloride, mp. 184°–190° C.

Example E10.

N-n-Propyl-3-[2,6-dimethylbenzoyloxy)-phenyl]piperidine hydrochloride (Method c)

A mixture of N-n-Propyl-3-(3-hydroxyphenyl)piperidine hydrobromide (1.0 g, 0.00033 mol) 2,6,-dimethylbenzoyl chloride (2.15 g, 0.0127 mol) and distilled dry pyridine (7 ml) was stirred at room temperature under N-atmosphere for 24 h. Aqueous NaHCO$_3$ was added and the mixture was extracted with ether. The organic phase was dried and all the solvents were evaporated giving an oily residue. The residue was eluted through an alumina column with ether and then through a silica gel column with light petroleum-ether (1:1) as eluant. The product was then precipitated by addition of HCl-saturated ether. Filtering and drying yielded 1.2 g (93%) of the pure desired hydrochloride, mp. 190°–191° C.

According to the methods of the Examples above, the following compounds were prepared and recrystallized as acid addition salts from ethanol/ether or isolated as the bases.

Example E11.

(—)-3-(3-Hydroxyphenyl)-N-n-propylpiperidine hydrochloride (Method j).

(—)-(3-Methoxyphenyl)-N-n-propylpiperidine hydrochloride (1.20 g, 0.0044 mol) in 48% aqueous HBr was heated at 120° for 4 h under N$_2$. The volatiles were removed in vacuo and the residue was recrystallized from methanol-ether giving (—)-3-(3-hydroxyphenyl)-N-n-propylpiperidine hydrobromide (1.10 g) mp. 166°–167° C.; $[\alpha]^{22}$D −5.8(C 2.0, CH$_3$OH). The hydrobromide was alkalinized with saturated NaHCO$_{33}$ (25 ml) and the mixture was extracted with ether (4×20 ml). The combined ether layers were dried (Na$_2$SO$_4$), filtered and HCl-saturated ether was added giving a precipitate which was recrystallized giving (—)-3-(3-hydroxyphenyl)-N-n-propylpiperidine hydrochloride (0.84 g, 75%), mp. 187°–188° C.; $[\alpha]^{22}$D −7.1 (C 2.2, CH$_3$OH).

Example E12.

(—)-3-(3-Hydroxyphenyl)-N-n-propylpiperidine hydrochloride (Method j).

(—)-3-(3-Methoxyphenyl)-N-n-propylpiperidine (1.50 g, 0.0064 mol) was dissolved in CH$_2$Cl$_2$ (25 ml) and cooled to −78°. BBr$_3$ (3.0 ml, 0.031 mol) was added under stirring. The cooling medium was removed and the mixture was allowed to reach room temperature. Alkalinization with excess 10% Na$_2$CO$_3$, extraction with CH$_2$Cl$_2$, drying (Na$_2$SO$_4$) and evaporation of the solvent gave a yellow oil (1.5 g). The oil was dissolved in abs. ethanol and excess of HCl-saturated ethanol was added. Evaporation to dryness followed by recrystallization from ether-ethanol gave (—)-3-(3-hydroxyphenyl)-N-n-propylpiperidine hydrochloride (1.05 g, 64%), mp. 187°–188° C.

Example E13.

(-)-N-n-Propyl-3-[3-(4-pivaloyloxybenzoyloxy)-phenyl]piperidine hydrochloride (Method 1).

(—)N-n-propyl-3-(3-hydroxyphenyl)piperidine hydrochloride (0.400 g, 1.56 mmol) was suspended in dry dichloromethane (4 ml). Pivaloyloxybenzoylchloride (0.413 g, 1.72 mmol) was dissolved in a mixture of dichloromethane (4 ml) and pyridine (0.136 g, 1.72 mmol). The solution was added to the suspension and the mixture was refluxed for 20 hours. The clear solution was cooled, washed with aqueous NaHCO$_3$ and dried with Na$_2$SO$_4$. After evaporation the residual oil was dissolved in ethanol, one equivalent HCl-saturated ethanol was added and the product precipitated by adding ether. Filtering and drying yielded 360 mg (50%) of the pure desired hydrochloride. Mp. 228°–229° C. $[\alpha]^{20}$D (C=1.5, MeOH) (—)9.05°.

Example E14.

(—)N-n-Propyl-3-(3-allyloxyphenyl)piperidine hydrochloride (method 1)

(—)N-n-propyl-3-(3-hydroxyphenyl)piperidine hydrochloride (0.255 g, 1 mmol) and tetrabutylammonium hydrogen sulphate (0.340 g, 1 mmol) were suspended in dichloromethane (2 ml) and allylbromide (0.133 g, 1.1 mmol). 2-M NaOH (2 ml) was added during two minutes and the mixture was stirred at room temperature for half an hour. The layers were separated and the organic layer was dried over Na$_2$SO$_4$. After removal of the solvent by distillation, the residual oil was dissolved in ether (50 ml). A theoretical quantity of tetrabutylammonium iodide was precipitated. The precipitate was filtered off and to the filtrate was added one equivalent HCl-saturated ether. White crystals of the desired compound was obtained. The crystals were filtered, washed on the filters with ether and dried. Yield 190 mg (65%). Mp. 136°–138° C. $[\alpha]^{20}$D (C=1.5 MeOH) (—)7.6°.

Example E15.

(—)-N-n-Propyl-3-(3-hydroxyphenyl)piperidine hydrochloride (Method k).

To a solution of the appropriate enantiomeric form of N-n-propyl-3-(3-aminophenyl)piperidine (0.27 g, 0.0013 mol) in 6M H$_2$SO$_4$ (1 ml) NaNO$_2$ (0.077 g, 0.0011 mol) dissolved in water (0.2 ml) was added dropwise at 5° C. and then the mixture was stirred at 5° C. for 1 h. The resulting mixture was added dropwise to refluxing 10% H$_2$SO$_4$ (1.5 ml) and the reflux was continued for 5 min. Cooling, alkalising (Na$_2$CO$_3$), extraction with ether, drying and evaporation of the organic phase gave the desired product as a free base. Conversion to the hydrochloride followed by recrystallization gave 0.059 g (20%) of (—)-N-n-propyl-3-(3-hydroxyphenyl)piperidine hydrochloride, m.p. 176°–177° C.

Example E16.

(—)-N-n-Propyl-3-(3-allyloxyphenyl)piperidine hydrochloride (Method n).

A solution of the appropriate enantiomeric form of N-n-propionyl-3-(3-allyloxyphenyl)piperidine (0.04 g, 0.16 mmol) in dried ether (5 ml) was dropped to a suspension of LiAlH$_4$ (0.04 g) in dried ether under nitrogen and stirring, and the mixture was refluxed for 30 min. H$_2$O (0.04 ml), 15% NaOH (0.04 ml) and H$_2$O (0.2 ml) were added and the precipitated crystals were filtered off and washed with ether. The solution was dried with Na$_2$SO$_4$. Evaporation to dryness gave an oily residue which was dissolved in ether. Addition of HCl-saturated ether resulted in precipitation of white crystals. The crystals were centrifuqated and treated with light petroleum, centrifugated and dried. Yield 0.02 g of the end compound having physical properties in accordance with Example E14.

Example E17.

(−)-(3-Decanoyloxyphenyl)-1-propylpiperidine hydrochloride (−)-3-(3-hydroxyphenyl)-1-propylpiperidine hydrochloride (1.5 g, 5.86 mmol) was suspended in dry dichloromethane (15 ml). Decanoylchloride (1.2 g, 6.29 mmol) was dissolved in a mixture of dichloromethane (15 ml) and pyridine (0.5 g, 6.32 mmol). The solution was added to the suspension and the mixture was refluxed for 20 hours. The clear solution was cooled, washed with aqueous NaHCO$_3$ and dried with Na$_2$SO$_4$. After evaporation the residual oil was dissolved in ether and precipitated as hydrochloride salt with one equivalent HCl in ether. The salt was recrystallized twice from acetone. Yield: 0.7 g (30%). M.p. 142°–144° C. [α]$^{20}$D (C-1.8, MeOH)=−5.6°, MS (70 eV): m/z 373 (5%), 344 (100%), 190 (7%).

Example E18.

A mixture of (−)N-propyl-3-(hydroxyphenyl) piperidine base (3.0 g; 0.0137 mol) in toluene (40 ml) and propylisocyanate (2.34 g; 0.0274 mol) was refluxed for 4 hours. The solution was evaporated and the residues were dissolved in ether. HCl-saturated ether was added giving white crystals. Filtration and recrystallisation from acetonitrile gave the desired compound, (−)N-propyl-3-[3-(propylcarbamoyloxy)-phenyl]piperidine. Yield: 75% m.p. 186°–188° C. [α]$^{20}$D=(−)7.85° [C=2.1; MeOH].

Example E19.

(−)N-propyl-3-[3-(diisopropylcarbamoyloxy)-phenyl]piperidine was prepared in analogy with the method for (−)N-propyl-3-[3-(piperidine-carbamoyloxy)phenyl]piperidine according to Example 3 from the corresponding diisopropylcarbamoylchloride. M.p. 193°–195° C. [α]$^{20}$D (−)5.59°.

Example E 20.

A solution of piperidinecarbonylchloride (4.03 g; 0.0273 mol) and (−)N-propyl-3-(hydroxyphenyl)piperidine (2.0 g; 0.0091 mol) in pyridine (25 ml) was stirred at 60° C. for 4 hours. The pyridine was evaporated carefully. The residue was washed with ether and tetrahydrofuran. Recrystallization from acetonitrile afforded the pure product (−)N-propyl-3(3-piperidinecarbonyloxphenyl)piperidine. Yield: 57% m.p. 209°–210° C. [α]$^{20}$D=(−)8.3° [C=2.1; MEOH].

Example E 21.

(−)N-propyl-3-[3-(3,4-dimethoxyphenylcarbamoyloxy) phenyl]-piperidine was prepared in accordance with Example 1. M.p. 183°–184° C., [α]$^{20}$D=1.28°.

Example E 22.

(−)N-propyl-3-[3-(p-chlorophenylcarbamoyloxy) phenyl]-piperidine was prepared in accordance with Example 1. M.p. 205°–208° C., [α]$^{20}$D −5.20°.

Example E 23.

(−)N-propyl-3-[3-p-isopropylcarbamoyloxy)-phenyl]piperidine was prepared in accordance with Example 1. M.p. 184°–185° C., [α]$^{20}$D=−6.91°.

Example E 24.

(−)N-propyl-3-[3-(p-tert.butylcarbamoyloxy)-phenyl]piperidine was prepared in accordance with Example 1. M.p. 179°–181° C. [α]$^{20}$D=−3.05°.

Example E 25.

(−)N-propyl-3-[3-(2-chloro-6-methylphenylcarbamoyloxy) p-phenyl]piperidine was prepared in accordance with Example 1. [α]$^{20}$D −4.43°.

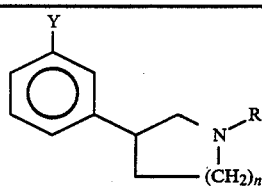

| Compound/Example No. | n | Y | R | Salt/Base | Method (Ref. to Example No.) | Melting point (°C.) or other data | Yield[a] % |
|---|---|---|---|---|---|---|---|
| Intermediates | | | | | | | |
| I8 | 2 | OCH$_3$ | H | HCl | A2, h | 137–138.5(*) | 93 |
|  | 2 | OCH$_3$ | CH$_3$ | HCl | A2, h (Ex. I6) | 153–154(*) | 68 |
|  | 2 | OCH$_3$ | C$_2$H$_5$ | HCl | A2, h (Ex. I6) | 149–150(*) | 46 |
| I2 | 1 | OCH$_3$ | n-C$_3$H$_7$ | base | A1, e | Bp 85–86/C.1(*) | 83 |
| I6 | 2 | OCH$_3$ | n-C$_3$H$_7$ | HBr | A2, h | 155–156(*) | 70 |
| I4 | 2 | OCH$_3$ | n-C$_3$H$_7$ | HCl | A1, d | 191 | 72 |
| I1 | 2 | OCH$_3$ | n-C$_4$H$_9$ | HCl | A1, e | 130–131(*) | 88 |
| I3 | 2 | OCH$_3$ | n-C$_5$H$_{11}$ | base | A1, d | NMR[b] | 25 |
|  | 2 | OCH$_3$ | —CH(CH$_3$)$_2$ | base | A1, d (Ex. I3) | NMR[d] | 43 |
|  | 2 | OCH$_3$ | —CH$_2$C(CH$_3$)$_3$ | base | A1, e (Ex. I1) | NMR[e] | 81 |
|  | 2 | OCH$_3$ | —CH$_2$CH=CH$_2$ | base | A1, d (Ex. I3) | NMR[f] | 30 |
|  | 2 | OCH$_3$ | —CH$_2$CH$_2$N(CH$_3$)(CH$_3$) | 2.HCl | A1, d (Ex. I3) | 165–170 dec.(*) | 64[o] |

-continued

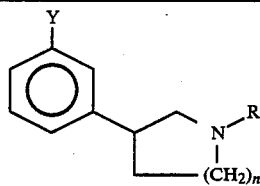

| Compound/Example No. | n | Y | R | Salt/Base | Method (Ref. to Example No.) | Melting point (°C.) or other data | Yield[a] % |
|---|---|---|---|---|---|---|---|
| | 1 | OCH$_3$ | —C(O)C$_2$H$_5$ | — | A1 (Ex. I2) | IR[g] | 100 |
| | 2 | OCH$_3$ | —C(O)C$_2$H$_5$ | — | A1 (Ex. I1) | IR[h] | — |
| | 2 | OCH$_3$ | —C(O)C$_3$H$_7$ | — | A1 (Ex. I1) | IR[i] | — |
| | 2 | OCH$_3$ | —C(O)C(CH$_3$)$_3$ | — | A1 (Ex. I2) | NMR, IR[j] | 91 |
| I9 | 2 | NH$_2$ | n-C$_3$H$_7$ | base | B2 | NMR[k] | |
| | | | End Compounds | | | | |
| 1 | 2 | OH | CH$_3$ | HBr | a (Ex. E1) | 169–170(*) | 70 |
| 2 | 2 | OH | C$_2$H$_5$ | HBr | a (Ex. E1) | 158–159(*) | 60 |
| 3 | 1 | OH | n-C$_3$H$_7$ | HBr | a (Ex. E1) | 128–129(*) | 80 |
| 4/E1 | 2 | OH | n-C$_3$H$_7$ | HBr | a | 146–147.5(*) | 86 |
| 5 | 2 | OH | n-C$_4$H$_9$ | HBr | a (Ex. E1) | 123–124(*) | 73 |
| 6/E2 | 2 | OH | n-C$_5$H$_{11}$ | HCl | a | 70–80,NMR[l] | 28 |
| 7 | 2 | OH | —CH(CH$_3$)$_2$ | HCl | a (Ex. E2) | 144–146 | 23 |
| 8 | 2 | OH | —CH$_2$C(CH$_3$)$_3$ | HCl | a (Ex. E2) | oil, NMR[n] | 14 |
| 9 | 2 | OH | —CH$_2$CH=CH$_2$ | HCl | a (Ex. E2) | 148–150 | 4 |
| 10/E3 | 2 | OC(O)CH$_3$ | n-C$_3$H$_7$ | HCl | c | 173–175 | 55 |
| 11 | 2 | OC(O)C(CH$_3$)$_3$ | n-C$_3$H$_7$ | HCl | c (Ex. E4) | 155 | 33 |
| 12/E4 | 2 | OC(O)C$_6$H$_5$ | n-C$_3$H$_7$ | HCl | c | 170 | 13 |
| 13/E5 | 2 | OH | —CH$_2$CH$_2$OH | HCl | d | 116.5–120 | 41 |
| 14 | 2 | OH | —CH$_2$CH$_2$N(CH$_3$)$_2$ | 2.HBr | a (Ex. E1) | 219–220 | 60 |
| 15/E6 | 2 | OH | n-C$_3$H$_7$ | HCl | b | 143.5–146 | 25 |
| 16/E7 | 2 | OCH$_2$CH=CH$_2$ | n-C$_3$H$_7$ | HCl | e | NMR[p] | 49 |
| 17/E8 | 2 | OCH$_2$C$_6$H$_5$ | n-C$_3$H$_7$ | HCl | c | 171 | 52 |
| 18/E9 | 2 | OC(O)NHC$_6$H$_5$ | n-C$_3$H$_7$ | HCl | c | 184–190 | 20 |
| 19/E10 | 2 | OC(O)-2,6-(CH$_3$)$_2$C$_6$H$_3$ | n-C$_3$H$_7$ | HCl | c | 190–191 | 93 |

-continued

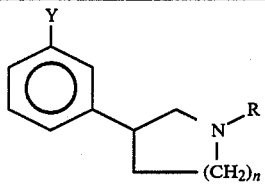

| Compound/ Example No. | n | Y | R | Salt/Base | Method (Ref. to Example No.) | Melting point (°C.) or other data | Yield[a] % |
|---|---|---|---|---|---|---|---|
| 20 | 2 | OC(=O)-C6H4-OCC(CH3)3 | n-C3H7 | HCl | c (Ex. E10) | 210–214 | 29 |
| 21 | 2 | OC(=O)-C6H5 | —CH(CH3)2 | HCl | c (Ex. E10) | 198–200 | 70 |
| 22 | 2 | OC(=O)-C6H5 | n-C4H9 | HCl | c (Ex. E10) | 82–85 | 62 |
| 23 | 1 | OH | —CH(CH3)2 | HBr | a (Ex. E1) | 146–148 | |
| 24 | 2 | OH | —CH2CH2CH2OH | | | | |
| 25 | 2 | OH | —CH2CH2CH2SCH3 | | | | |
| 26 | 2 | OH | —CH(CH2CH3)2 | | | | |

Footnotes
(*)Submitted for elemental analysis (C,H,N); All the analyses were satisfactory.
[a]Calculated on the starting phenylpiperidine or pyridinylbenzene.
[b]δ(CDCl3) 0.7–3.2 (20H,m), 3.75 (3H,s), 6.6–7.0 (3H,m), 7.0–7.4 (1H,m).
[c]δ(CDCl3) 0.7–3.2 (26H,m), 3.75 (3H,s), 6.6–6.95 (3H,m), 6.95–7.35 (1H,m).
[d]δ(CDCl3) 1.0 (6H,d), 1.0–3.1 (10H,m), 3.7 (3H,s), 6.55–6.95 (3H,m), 6.95–7.35 (1H,m).
[e]δ(CDCl3)1.2 (9H,s), 1.2–3.1 (11H,m), 3.7 (3H,s) 6.6–6.9 (3H,m), 6.9–7.35 (1H,m).
[f]δ(CDCl3) 1.3–3.3 (11H,m), 3.8 (3H,s), 4.9–5.4 (2H,m), 5.55–6.3 (1H,m), 6.6–7.0 (3H,m), 7.0–7.4 (1H,m).
[g]νmax 1680 (C=O), 1260 (ArOCH3)
[h]νmax 1640 (C=O), 1250 (ArOCH3)
[i]νmax 1638 (C=O), 1255 (ArOCH3)
[j]δ(CDCl3) 1.3 (9H,s), 1.4–3.0 (9H,m), 3.8 (3H,s), 6.65–6.95 (3H,m), 7.1–7.45 (1H,m); νmax 1650 cm$^{-1}$.
[k]δ(CDCl3) 0.9 (3H,t), 1.15–3.25 (13H,m), 3.5 (2H, br.s), 6.4–6.75 (3H,m), 6.95–7.3 (1H,m).
[l]δ(CDCl3) 0.7–3.5 (20H,m), 6.6–6.9 (3H,m), 6.9–7.35 (1H,m), 9.8(1H,br.s).
[m]δ(CDCl3) 0.7–3.4 (26H,m), 6.55–6.9 (3H,m) 6.9–7.3 (1H,m), 9.55 (1H, br.s).
[n]δ(CD3OD) 1.1 (9H,s), 1.7–3.6 (11H,m), 5.1 (1H, br.s), 6.6–6.95 (3H,m), 6.95–7.35 (1H,m).
[o]by using dimethyl-2-chloroethylamine hydrochloride as alkylating agent.
[p]δCDCl3 0.92 (3H,t), 1.2–3.2 (16H,m), 4.45–4.65 (2H,m), 5.15–5.30 (1H,m), 5.30–5.60 (2H,m), 5.80–6.40 (1H,m), 6.55–6.90 (3H,m), 7.00–7.35 (1H,m).

The following examples illustrate how the compounds of the present invention may be included into pharmaceutical preparations.

Example P1.

Preparation of soft gelatine capsules 500 g of active substance are mixed with 500 g of corn oil, whereupon the mixture is filled in soft gelatine capsules, each capsule containing 100 mg of the mixture (i.e. 50 mg of active substance).

Example P2.

Preparation of tablets 0.5 kg of active substance are mixed with 0.2 kg of silicic acid of the trade mark Aerosil 0.45 kg of potato starch and 0.5 kg of lactose are mixed therewith and the mixture is moistened with a starch paste prepared from 50 g of potato starch and distilled water, whereupon the mixture is granulated through a sieve. The granulate is dried and sieved, whereupon 20 g of magnesium stearate are mixed into it. Finally, the mixture is pressed into tablets each weighing 172 mg.

Example P3.

Preparation of a syrup 100 g of active substance are dissolved in 300 g of 95% ethanol, whereupon 300 g of glycerol, aroma and colouring agents (q.s.) and 1000 ml of water are mixed therein. A syrup is obtained.

Example P4.

Preparation of an injection solution

Active substance (hydrobromide) (1 g), sodiumchloride (0.8 g) and ascorbic acid (0.1 g) are dissolved in sufficient amount of distilled water to give 100 ml of solution. This solution, which contains 10 mg of active substance per ml, is used in filling ampoules, which are sterilized by heating at 120° C. for 20 minutes.

Pharmacological evaluation

A. Substituted Phenylazacycloalkanes

Drugs acting on central dopamine (DA) transmission have for long been known to be clinically effective in a variety of diseases originating in the CNS, e.g. parkinsonism and schizophrenia. In the former condition, the nigro-neostriatal hypofunction can be restored by an increase in postsynaptic DA-receptor stimulation, whereas the latter condition can be normalized by achieving a decrease in postsynaptic DA-receptor stimulation. So far, this decrease has been mainly accomplished either by (a) direct blockade of the postsynaptic DA receptors (considered to be the mode of action for classical antipsychotic agents like e.g. haloperidol and chlorpromazine) or (b) inhibition of intraneuronal presynaptic events essential for the maintenance of adequate neurotransmission, e.g. granular uptake and storage (cf. the neuroleptic reserpine, which is known to deplete the monoamine stores via its actions upon granular structures), transport mechanisms and transmitter synthesis.

In recent years a large body of pharmacological, biochemical and electrophysiological evidence has accumulated, providing considerable support in favor of the existence of a specific population of central autoreculatory DA receptors, so-called autoreceptors, located on the dopaminergic neuron itself (i.e. presynaptically located). These receptors are part of a homeostatic mechanism that modulates nerve impulse flow and transmitter synthesis and thus the amount of DA released from the nerve endings.

The well-known direct DA-receptor agonist apomorphine is able to activate the DA autoreceptors as well as the postsynaptic DA receptors. At low doses, however, the effects of autoreceptor stimulation appear to predominate, whereas at higher doses the (autoreceptor-mediated) attenuation of DA transmission is outweighed by the enhancement in postsynaptic receptor stimulation. Thus, the "paradoxical" antipsychotic and antidyskinetic effects demonstrated in man after low doses of apomorphine are most probably to be attributed to the autoreceptor-stimulatory properties of this DA-receptor agonist. In accordance with this, and in view of current knowledge of the drawbacks linked to the use of DA-receptor antagonists in the therapy of schizophrenia and other psychotic disorders, it has been suggested that DA-receptor stimulants with a high selectivity for CNS DA autoreceptors would offer new therapeutic principles of great value in psychiatric medicine. At the moment no such drug is commonly known. While searching for new postsynaptic DA-receptor agonists (anti-Parkinson agents), we surprisingly discovered a group of substances possessing selective DA-autoreceptor agonistic properties. In order to investigate this new pharmacological profile, the following experiments were performed. For compound numbers see table of "End Compounds" above.

Pharmacological procedures

1. Antagonism of the reserpine-induced "neuroleptic syndrome" in the rat

Depletion of the monoamine stores with reserpine brings about a "neuroleptic syndrome" characterized by hypomotility, catalepsy, muscle rigidity, hunch-backed posture as well as a number of other central and peripheral signs of monoamine depletion. This syndrome can be reversed by the administration of drugs that stimulate postsynaptic DA receptors directly or indirectly, e.g. apomorphine, L-Dopa.

Rats (150–300 g) pretreated with reserpine (10 mg/kg i.p., 6 h before) were given compound 4 subcutaneously at different doses. However, no antagonism of the reserpine-induced syndrome was observed, not even at nearly lethal doses. In a similar manner, compound 7 was tested at 20 mg/kg s.c., i.e. a dose about 100 times the $ED_{50}$ in Table I. No antagonism of the reserpine-induced syndrome was seen.

2. In-vivo determination of rat brain tyrosine hydroxylation.

The compounds under evaluation were tested biochemically for central DA-receptor (pre- and/or postsynaptic) stimulating activity. The concept of this biochemical screening method is that a DA-receptor agonist will stimulate the receptor and through regulatory feedback systems effect a decline in tyrosine hydroxylase activity and thus a subsequent reduction in the synthesis rate for DA in the presynaptic neuron. Dopa formation, as determined after in-vivo inhibition of the aromatic L-amino acid decarboxylase with NSD 1015 (3-hydroxybenzyl-hydrazine hydrochloride), is taken as an indirect measure of DA synthesis rate.

Rats (150–300 g) pretreated with reserpine were given the compounds under evaluation. Gross behavioral observations (changes in motility, stereotypies etc.) were made in order to evaluate possible postsynaptic dopamine receptor activity. Subsequent administration of NSD 1015, decapitation, brain dissection (corpora striate and the limbic fore-brain), homogenization, centrifugation, ion-exchange chromatography and spectrofluorimetric measurements (all as described in detail by Wikstrom et al., in J. Med. Chem. 21, 864–867, 1978, and references cited therein), gave the actual Dopa levels. Several doses (n=4–6) were tested in order to obtain dose-response curves for each compound and brain area. The dose of a compound producing a half-maximal decrease in the Dopa level in the rat brain part was then estimated. These values ($ED_{50}$) are presented in Table I.

From studies on many other compounds having autoreceptor activity as well as postsynaptic activity we know that at a dose representing the $ED_{50}$ value only autoreceptor activation is likely to occur. To obtain postsynaptic activation higher doses are necessary. (At the moment no compound with selective postsynaptic DA-stimulating activity is known.) Therefore, independently of other presented evidence (above or below) concerning receptor selectivity, the $ED_{50}$ values are considered to represent doses eliciting selective autoreceptor stimulation.

All the compounds in Table I were biochemically active except for the two reference compounds tested, which were completely inactive even at 180 mol/kg and 90 mol/kg, respectively. Most of the active compounds have a potency of approximately the same order ($ED_{50}$ 0.6–4.4). These compounds are considered to be the most suitable for medical use. Compounds with an $ED_{50}$ value of about 45 mol/kg as for N-propyl-30(3-hydroxyphenyl)pyrrolidine may be considered to be of borderline interest.

The absence of significant postsynaptic DA-receptor activation at any dose tested indicates that all the active compounds have selectivity for the autoreceptors (further investigated only for compound 4).

3. Antagonism of γ-butyrolactone (GBL)-induced increase in rat brain DA synthesis rate.

The administration of GBL in anesthetic doses inhibits nerve impulse flow in central DA neurons, thus resulting in a loss of the impulse-mediated feedback control of tyrosine hydroxylase activity and in a subsequent increase in transmitter synthesis rate (which is determined as described under 2 above). Since the GBL inhibition precludes neuronal feedback actions, antagonistic effects exerted by DA-receptor agonists upon the GBL-induced increase in synthesis are in all probability to be ascribed to their stimulating the DA autoreceptors present in the terminal area of the DA neurons.

Rats (150–300 g), were given compound 4 subcutaneously at several doses (n=7) followed by GBL (750 mg/kg i.p., 5 min. later) and NSD 1015 (100 mg/kg i.p., 10 min. later). By a subsequent procedure according to 2 above the Dopa levels (representing the DA-synthesis rates) were determined. In this model compound 4 dose-dependently antagonized the GBL-induced increase in DA synthesis rate (Logarithmically adjusted dose-response data in Table II). The maximal reversal of the GBL-induced increase in DA synthesis rate was approximately 160% in the limbic system and 110% in corpus striatum. Furthermore, the antagonism could be blocked by haloperidol, hence confirming that the effects are due to actions on DA autoreceptors (Table III).

4. Effect on spontaneous locomotor activity in the rat.

Untreated animals exposed to a new environment display an initial high motor activity which then gradually declines over a period of time. Administration of DA-receptor agonists (e.g. apomorphine) in doses where preferential autoreceptor stimulation is likely to occur, causes a depression of the spontaneous motility mentioned above, considered to be due to the DA autoreceptor-mediated impairment of central DA transmission.

Rats (150–300 g) were injected subcutaneously with several doses of compounds 4 and after 5 minutes they were individually placed in motility boxes ("M/P 40 Fc Electronic Motility Meter". Motron Products, Stockholm) and the motor activity (0–30 min.) was quantified. Compound 4 exhibits a clear dose-dependent decrease of the initial high motor activity, the maximal effect, being a 75% decrease from control values, attained at about 8 mg/kg. No locomotor stimulation was ever seen, regardless of the dose used. Pretreatment with a low dose of haloperidol (0.02 mg/kg i.p., 30 min. before), in order to selectively block DA-autoreceptor sites, at least partly reversed the sedative effect obtained with a low dose (0.5 mg/kg) of compound 4 (Table IV). Moreover, there seems to be a correlation between the decrease in spontaneous locomotion and the degree of antagonism of the GBL-induced increase in DA synthesis (cf. 3 above) in the limbic areas of rat brain exerted by compound 4, the per cent decrease of motor activity being roughly 0.6 times the per cent reversal of GBL-induced increase in DA-synthesis rate.

5. Turning behavior in rats with acute unistriatal lesion.

In animals with an acute unilateral KCl-lesion (1μl 25% KCl lesioned side, 1μl 20% NaCl control site, administered through previously implanted "guide cannulaes") of the striatum, compensatory counterbalancing adjustments in the intact contralateral striatum are brought about and therefore no appreciable asymmetry in body posture or torsion is observed. Disturbances in the balance produces, depending on the point of attack, ipsi- or alternatively contralateral turning. In this model postsynaptically active DA agonists (e.g. apomorphine, high dosage) elicit ipsilateral turning and rotatory behavior whereas DA antagonists (e.g. haloperidol) cause contralateral turning. Consequently it could be expected that agents acting exclusively on DA autoreceptors would produce contralateral turning in the lesioned animals.

Rats (150–300 g) pretreated as above were given compound 4 subcutaneously at several dose levels and then the animals were observed for at least 4 h. As predicted herein, it was demonstrated that compound 4, in each dose tested, made the animals turn to the side contralateral to the lesion (Table V). Moreover, their overall appearance was indicative of a sedative action exerted by compound 4, thus corroborating the previous findings (cf. 4 above). It was also shown that the ipsilateral turning and rotatory response after administration of postsynaptically effective doses of apomorphine (1.0 mg/kg s.c.) was not affected by pretreatment with compound 4 (Table V).

6. Other observations.

Further preliminary investigations on the pharmacological profile of compound 4 have indicated that it, in contrast to agents stimulating postsynaptic DA receptors, is devoid of emetic activity in dogs (at least at 1 mg/kg i.m.). As opposed to postsynaptically acting DA agonists, compound 4 (8 mg/kg s.c.) also failed to lower the rat rectal temperature (0–30 min ). It was in fact lacking any measurable temperature effects.

7. A comparative study of compound 4 and its 3,4-dihydroxy-analogue known from DE Offenlequngsschrift No. 2 621 536.

Rats (150–300 g) pretreated with reserpine (10 mg/kg i.p., 6 h before) were given either phys. saline, compound 4 (100 μmol/kg), N-n-propyl-3-(3,4-dihydroxyphenyl)piperidine (100 μmol/kg) or apomorphine (2 mol/kg) subcutaneously and the locomotor activity (accumulated counts 0–60 min.) was quantified by means of Motron boxes (see under 4 above). The results (Table VI) show that, apart from their DA-autoreceptor actions ($ED_{50}$:s; cf, 2 above), N-n-propyl-3-(3,4dihydroxyphenyl)piperidine as well as apomorphine, exhibit strong central postsynaptic DA-receptor stimulatory effects. In contrast to the latter agonists, compound 4 appeared to selectively act on the DA autoreceptors and hence failed to elicit a motor response that differed more than slightly from control values.

III. New Enantiomers of substituted phenylazacycloakanes

Among the compounds described in EP-A1-0030526, the compound N-n-propyl-3-(3-hydroxyphenyl)-piperidine, hereinafter referred to as 3-PPP, was presented in greatest detail.

It was shown that 3-PPP and its congeners are capable of inhibiting the physiological activity of central dopaminergic neurons by activating a subpopulation of dopaminergic receptors presumably located on the dopaminergic neuron itself, i.e. presynaptic receptors or autoreceptors. The effect proved to be selective, in that no concomitant activation of the classical postsynaptic dopaminergic receptors could be detected.

These observations were made on racemic mixtures. The two enantiomers of 3-PPP have now been tested separately. Surprisingly the levorotatory enantiomer, (−)-3-PPP, not only was capable of activating the presynaptic dopaminergic receptors (autoreceptors) but concomitantly reduced the sensitivity of the postsynaptic dopaminergic receptors to dopaminergic agonists. By the combined activation of presynaptic receptors and partial blockade of postsynaptic receptors the inhibitory action on dopaminergic neurotransmission will be stronger than by either effect alone. In other words, the levorotatory enantiomer is superior to the racemic mixture as an inhibitor of dopaminergic neurotransmission by acting both presynaptically as an agonist and postsynaptically as an antagonist.

The reason for the difference in pharmacological profile between the levorotatory enantiomer and the racemic mixture has been clarified: the dextrorotatory enantiomer was found to be a dopaminergic receptor agonist by activating both the presynaptic and the postsynaptic receptors. Thus, the two enantiomers antagonize each other on the postsynaptic dopaminergic receptor. As a consequence, the racemic mixture will be active only on the presynaptic receptor (autoreceptor). The pharmacological tests demonstrating the properties of the two enantiomers of 3-PPP are presented below.

1. Evidence for presynaptic dopaminergic receptor (autoreceptor) agonist activity of both enantiomers of 3-PPP.

Both enantiomers of 3-PPP cause a dose-dependent decrease in spontaneous exploratory motor activity of rats. In male Sprague-Dawley rats injected subcutaneously with either enantiomer of 3-PPP and 5 min later placed in Motron boxes for measurement of motor activity the number of counts during the first 30 min was recorded at doses between 0.053 and 64 mg/kg. Both enantiomers cause a decrease of locomotor activity to 30–40% of control. However, the (+)-enantiomer causes a decrease only after doses between 0.25 and 4 mg/kg s.c. After 8 mg/kg there is no effect, and after 64 mg/kg there is a significant increase to more than 200% of control. In contrast, the (−)-enantiomer causes a decrease after all these doses, with no reversal of the effect after larger doses.

In the dopaminergic neurotransmission L-tyrosine is hydroxylated to L-dopa, which is decarboxylated to the transmitter substance dopamine. After inhibition of the aromatic amino acid decarboxylase by means of 3-hydroxybenzylhydrazine HCl (NSD 1015) both enantiomers of 3-PPP cause a dose-dependent decrease at doses between 0.053 and 64 mg/kg in the formation of dopa in dopamine-rich brain regions of rats pretreated with reserpine or gammabutyrolactone (GBL). Pretreatment with GBL and probably also reserpine precludes the influence of postsynaptic dopamine receptors on dopa formation and thus provides the opportunity to study the influence of presynaptic autoreceptors separately (cf. Hjorth et al., Life Sci. Vol. 28, pp. 1225–1238, 1981). The effect of both enantiomers on dopa formation is blocked by the dopamine-receptor antagonist haloperidol. These finds provide strong evidence for stimulation of presynaptic dopamine receptors (autoreceptors).

In rats not pretreated with GBL or reserpine the two enantiomers act differently on dopa formation at doses between 0.053 and 64 mg/kg: the (+)-form causes a decrease, whereas the (−)-form causes an increase in dopa formation in the striatum and no change in the limbic region. These changes in dopa formation are matched by corresponding changes in the levels of the dopamine metabolites 3,4-dihydroxyphenyl acetic acid and homovanillic acid. This differential action of the two enantiomers will be commented on below.

2. Evidence for postsynaptic dopaminergic receptor agonist activity of (+)-3-PPP.

In reserpine-treated rats (+)-3-PPP causes a marked stimulation of locomotor activity at doses between 0.25 and 64 mg/kg. The effect is blocked by haloperidol. These findings provide strong evidence for a stimulating action of (−)-form causes only a very weak stimulation of motor activity in reserpine-pretreated rats, indicating virtual absence of stimulating action on postsynaptic dopaminergic receptors.

3. Evidence for postsynaptic dopminergic receptor antagonist activity of (−)-3-PPP.

The locomotor stimulating action of the dopamine receptor aqonist apomorphine is antagonized by (−)-3-PPP. This effect is clearcut after a dose of 8 mg/kg s.c. of (−)-3-PPP, but not after 2 mg/kg. Thus the postsynaptic receptor antagonist activity requires a larger dose than the presynaptic receptor agonist activity, which is evident after doses down to 0.25 mg/kg. The above-mentioned ability of (−)-3-PPP to stimulate dopa formation and to raise dopaminemetabolite levels in rat striatum provides further evidence for blockade of postsynaptic dopamine receptors, resulting in feedback-mediated stimulation of dopaminergic neurons.

Further, (−)-3-PPP and racemic 3-PPP have been compared regarding antagonism of apomorphine-induced locomotor stimulation. Either form of 3-PPP was injected subcutaneously in a dose of 8 mg/kg 20 min and apomorphine in a dose of 1 mg/kg subcutaneously 5 min before placing the rats in the Motron for 30 min. Shown are the counts per 30 min., means± s.e.m. and number of experiments (n). As demonstrated in Table 1 (−)-3-PPP antagonized said stimulation while the racemate did not.

The (−)-form of 3-PPP has a striking antagonistic action against the locomotor stimulating activity of (+)-amphetamine. This effect is probably the result of the simultaneous stimulation of presynaptic dopaminergic receptors and partial blockade of postsynaptic dopaminergic receptors. All the major antipsychotic agents in current use are potent amphetamine antagonists, and such activity is considered to be predictive of antipsychotic action.

The compounds of the invention are believed to exert their main activity after metabolism to the corresponding compound of formula bII above. Thus the compounds of the invention are believed to be prodrugs or bioprecursors of said compound of formula bII. The compounds of the invention possess an improved oral absorption as compared with the compound of formula II and other previously described compounds.

CONCLUSION

The pharmacological data affirm the hypothesis that the compounds under consideration are centrally acting selective DA autoreceptor stimulating agents, and thus of great clinical interest in the treatment of psychotic disorders such as schizophrenia and a number of other disease states such as tardive dyskinesia, Huntington's chorea, hypoprolactinemia, alcoholism and drug abuse, said psychotic disorders and other disease states possibly being associated with a pathological increase in central DA transmission.

Extrapyramidal motor disturbances of choreatic type are avoided with the enantiomer compounds of the invention. As compared with the racemates, the pure enantiomers of the invention have a better efficacy in the suggested treatment in having an unexpected postsynaptic dopamine antagonist activity in addition to the presynaptic dopamine antagonist activity.

TABLE I

| Compound No. | n | Y | R' | Salt Base | ED$_{50}$* (μmol/kg s.c.) Limbic | Striatum |
|---|---|---|---|---|---|---|
| 1 | 2 | OH | CH$_3$ | HBr | 2.1 | 1.5 |
| 2 | 2 | OH | C$_2$H$_5$ | HBr | 4.4 | 4.2 |
| 3 | 1 | OH | n-C$_3$H$_7$ | HBr | ~45 | ~45 |
| 4[3] | 2 | OH | n-C$_3$H$_7$ | HBr | 2.7 | 2.7 |
| 5 | 2 | OH | n-C$_4$H$_9$ | HBr | 1.7 | 0.7 |
| 6 | 2 | OH | n-C$_5$H$_{11}$ | HCl | 0.9 | 0.6 |
| 7[3] | 2 | OH | —CH(CH$_3$)$_2$ | HCl | 0.8 | 0.7 |
| 9 | 2 | OH | —CH$_2$CH=CH$_2$ | HCl | 4.2 | 4.0 |
| 10 | 2 | —OCCH$_3$ (O) | n-C$_3$H$_7$ | HCl | 1.2 | 1.5 |
| 11 | 2 | —OCC(CH$_3$)$_3$ (O) | n-C$_3$H$_7$ | HCl | 2.2 | 1.7 |
| 12[3] | 2 | —OCC$_6$H$_5$ (O) | n-C$_3$H$_7$ | HCl | 1.8 | 2.0 |
| 13 | 2 | OH | —CH$_2$CH$_2$OH | HCl | ~20 | ~20 |
| 14 | 2 | OH | —CH$_2$CH$_2$N(CH$_3$)$_2$ | 2-HBr | ~20 | ~20 |
| 16[3] | 2 | OCH$_2$CH=CH$_2$ | n-C$_3$H$_7$ | HCl | <45 | <45 |
| 17[3] | 2 | 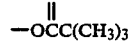 | n-C$_3$H$_7$ | HCl | <45 | <45 |
| 18 | 2 |  | n-C$_3$H$_7$ | HCl | <45 | <45 |
| 19[3] | 2 | 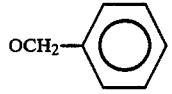 | n-C$_3$H$_7$ | HCl | <45 | <45 |
| 20[3] | 2 | 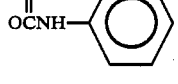 | n-C$_3$H$_7$ | HCl | <45 | <45 |
| 21[3] | 2 | 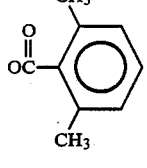 | —CH(CH$_3$)$_2$ | HCl | 0.5 | 0.5 |
| 22 | 2 | 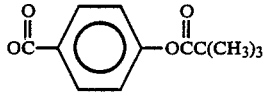 | n-C$_4$H$_9$ | HCl | <2.7 | <2.7 |
| 23 | 1 | OH | —CH(CH$_3$)$_2$ | HBr | | |

TABLE I-continued

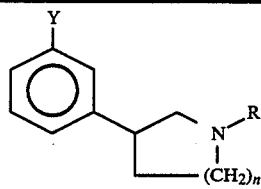

| Compound No. | n | Y | R' | Salt Base | ED$_{50}$* (μmol/kg s.c.) Limbic | Striatum |
|---|---|---|---|---|---|---|
| | 2 | —OCH$_3$ | n-C$_3$H$_7$ | HBr | I$^{(1)}$ | I$^{(1)}$ |
| | 1 | —OH | H | HBr | I$^{(2)}$ | I$^{(2)}$ |

I = inactive.
$^{(1)}$ED$_{50}$ >180 μmol/kg.
$^{(2)}$ED$_{50}$ >90 μmol/kg.
*Gross behavioural observations revealed no significant postsynaptic DA-receptor activation.
$^{(3)}$Also tested with oral administration in the rat at 180 μmol/kg without pretreatment with reserpine. All the compounds tested were active in reducing dopa accumulation.

TABLE II

% Reversal of GBL-induced increase in dopamine synthesis rate

| Compound 4 mg/kg s.c. | Limbic system | Corpus strietum |
|---|---|---|
| 0.5 | 58 | 0 |
| 1.0 | 75 | 17 |
| 2.0 | 92 | 34 |
| 4.0 | 109 | 51 |
| 8.0 | 126 | 68 |
| 16.0 | 142 | 86 |

TABLE III

Blockade of compound 4-induced reversal of the GBL-elicited increase in DA synthesis rate.

| Treatment | Dopa concentration ng per g tissue Limbic system | Striatum | Number of animals |
|---|---|---|---|
| Control (NaCl) | 307 ± 13 | 660 ± 40 | 18 |
| Control (GBL) | 506 ± 24 | 2366 ± 103 | 18 |
| Compound 4(32 mg/kg s.c.)- GBL | 191 ± 16$^1$ | 1063 ± 74$^1$ | 5 |
| Haloperidol(1 mg/kg i.p.)-(32 mg/kg compound 4) | 387 ± 32$^2$ | 2193 ± 53$^2$ | 3 |

$^1$Significant, p < 0.001 versus GBL-control values (B).
$^2$Not significant, p < 0.05 versus GBL-control values (B).

TABLE IV

Antagonism of the compound 4-induced depression of locomotor activity in rats.

| Treatment | Motor activity (acc. counts 0–15 min) | Number of animals |
|---|---|---|
| Glucose (i.p., 25 min before measurement) + physiological saline (s.c. 5 min before measurement) | 117 ± 17 | 6 |
| Haloperidol (0.02 mg/kg i.p., 25 min before measurement) + physiological saline (s.c., 5 min before measurement) | 140 ± 22 | 5 |
| Glucose (i.p., 25 min before measurement) + compound 4 (0.5 mg/kg s.c., 5 min before measurement) | 43 ± 9 | 5 |
| Haloperidol (0.02 mg/kg i.p., 25 min before measurement) — compound 4 (0.5 mg/kg s.c., 5 min before measurement) | 80 ± 10$^1$ | 7 |

$^1$Significantly different from group C, p < 0.025.

TABLE V

Turning behaviour in rats with acute unistriatal KCl lesion. Compound 4

| Dose (mg/kg s.c.) | Number of animals | Turning Ipsi lateral | Contra lateral | Catalepsy$^a$ | Duration of turning | Apomorphine-$^c$ induced turning |
|---|---|---|---|---|---|---|
| 32 | 8 | 0 | 8 | + | >4 h | Ipsi 8/8 |
| 8 | 4 | 0 | 4 | — | >4 h | Ipsi 4/4 |
| 4 | 2 | 0 | 2 | — | NT$^b$ | NT |
| 2 | 4 | 0 | 4 | — | >2 h | Ipsi 4/4 |
| 1 | 2 | 0 | 2 | — | NT | NT |

$^a$+ present, — absent
$^b$NT = not tested
$^c$apormorphine 1.0 mg/kg s.c. injected 1 h after compound 4.

TABLE VI

Comparison of compound 4 with two known dopaminergic agonists.

| Treatment | Motor activity (acc. counts 0–60 min postinj.) | Number of animals | ED$_{50}$ (μmol/kg s.c.) (cr. table 1) Limbic | Striatum |
|---|---|---|---|---|
| Control (0.9% saline) | 15 ± 5 | 4 | — | — |
| Compound 4 (100 μmol/kg s.c.) | 55 ± 4 | 3 | 2.7 | 2.7 |

TABLE VI-continued

| | Comparison of compound 4 with two known dopaminergic agonists. | | | |
|---|---|---|---|---|
| Treatment | Motor activity (acc. counts 0–60 min postinj.) | Number of animals | $ED_{50}$ ($\mu$mol/kg s.c.) (cr. table 1) Limbic | Striatum |
| N-n-propyl-3-(3',4'-dihydroxy-phenyl)-piperidine (100 $\mu$mol/kg s.c.) | 522 ± 83 | 3 | 9.4 | 10.0 |
| Apomorphine (2 $\mu$mol/kg s.c.) | 624 ± 51 | 4 | 0.19 | 0.22 |
| | Antagonism of apomorphine-induced locomotor stimulation. | | | |
| Vehicle (control) | 174 ± 15 | | (10) | |
| Apomorphine | 513 ± 35 | | (10)[a] | |
| (−)-3-PPP + Apomorphine | 276 ± 50 | | (5)[b] | |
| (±)-3-PPP + Aporrmorphine | 443 ± 26 | | (5)[c] | |

[a]differs from control, p<0.001
[b]differs from apomorphine, p<0.005
[c]not significantly different from apomorphine.

Best Mode of Carrying Out the Invention

The compound N-n-propyl-3-(3-hydroxphenyl)-piperidine and its pure enantiomer (−)-N-n-propyl-3-3(3-hydrophenyl) piperidine and its salts, processes for preparing said compound and methods of employing said compound in therapy represent the best mode of carrying out the invention known at present. Other compounds of great value are N-butyl-3-(3-hydroxphenyl)piperidine, N-pentyl-3-(3-hydroxphenyl)piperidine, and N-isopropyl-3-(3-hydroxphenyl)piperidine.

We claim:

1. A process for the preparation of a compound of the formula

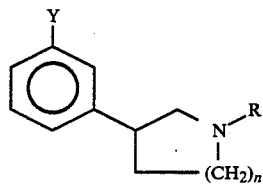

wherein n is 2, Y is OH, $R^1COO$, $R^2R^3NCOO-$ or $R^4O$ and wherein $R^1$ is an alkyl group having 1–5 carbon atoms or a substituted phenyl group, $R^2$ is an alkyl group having 1–5 carbon atoms, a phenethyl, benzyl or phenyl group, $R^3$ is H or an alkyl group having 1–5 carbon atoms and $R^4$ is an allyl or benzyl group, an dR is an alkyl group having 1–5 carbon atoms, an hydroxyalkyl, dimethylaminoalkyl or methylthioalkyl group having 2–6 carbon atoms in the alkyl part and having the heteroatom bound in a position other than the 1 position, an alkenyl group having 3–5 carbon atoms other than a 1-alkenyl group, as the base or pharmaceutically acceptable acid addition salt thereof, comprising the steps of (a) hydrogenating a compound of the formula

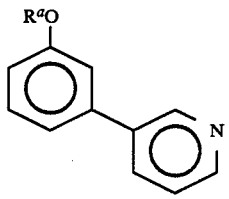

to form a first intermediate compound of the formula

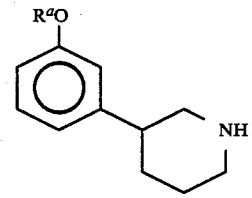

wherein $R^a$ is an alkyl group of from 1–5 carbon atoms or an acyl group of from 2–6 carbon atoms;

(b) reacting the first intermediate compound with an alkylating group selected from the group consisting of alkyl halides, hydroxyalkyl halides, dimethylaminoalkyl halides, methylthioalkyl halides, alkenyl halides, benzyl halides, alkyl tosylates, hydroxyalkyl tosylates, dimethylaminolakyl tosylates, methylthioalkyl tosylates, alkenyl tosylates, benzyl tosylates, carboxylic acid-sodium borohydride complexes of the formula $R^bCOOH-NaBH_4$, wherein $R^bCH_2-$ equals $R^1$, 2epoxy alkanes and a mixture of formaldehyde and $Na(CN)BH_3$ to form a second intermediate compound of the formula

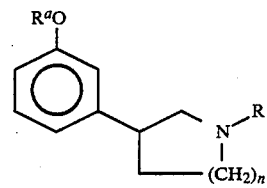

and (c) cleaving the ether or ester bond of the second intermediate compound to form a compound of formula I wherein Y is a hydroxy group.

2. A method according to claim 1, further comprising the step of reacting the hydroxy compound of step (c), with a carboxylic acid halide $R^1COX$ or anhydride $(R^1CO)_2O$ to form a compound of formula I wherein Y is $R^1COO-$.

3. A method according to claim 1, further comprising the steps of reacting the hydroxy compound of step (c) with a carbamoyl halide $R^2R^3NCOX$ or isocyanate $R^2NCO$ in the presence of a base or acid to form a compound of formula I wherein Y is $R^2R^3NCOO-$.

4. A method according to claim 1, further comprising the step of reacting the hydroxy compound of step (c) with an allyl or benzyl halide $R^4X$ in the presence of a base to form a compound of formula I wherein Y is $R^4O-$.

5. A method according to claim 1, wherein the compound hydrogenated in step (a) is a single purified optical isomer and the compound produced by step (c) is a single purified optical isomer.

6. A method according to claim 2, wherein the compound hydrogenated in step (a) is a single purified optical isomer and the compound produced by step (c) is a single purified optical isomer.

7. A method according to claim 3, wherein the compound hydrogenated in step (a) is a single purified optical isomer and the compound produced by step (c) is a single purified optical isomer.

8. A method according to claim 4, wherein the compound hydrogenated in step (a) is a single purified optical isomer and the compound produced by step (c) is a single purified optical isomer.

* * * * *

UNITED STATES PATENT AND TRADEMARK OFFICE
CERTIFICATE OF CORRECTION

PATENT NO. : 4,937,346

DATED : June 26, 1990

INVENTOR(S) : Arvidsson et al.

It is certified that error appears in the above-identified patent and that said Letters Patent is hereby corrected as shown below: On the title page and Col. 1, line 1;
[54], "PHENYL-AZACYKLOALKANES" should read --PHENYL-AZACYCLOALKANES--;
Col. 1, line 1, "PHENYL-AZACYKLOALKANES" should read --PHENYL-AZACYCLOALKANES--;
Col. 3, line 45, "neuropharmacoloqical" should read --neuropharmacological--;
Col. 7, line 21, "or $C_2H_5-S^{31}$" should read --or $C_2H_5-S^-$--;
Col. 7, line 36, "NH ," should read --$NH_2$,--;
Col. 8, line 22, "is the" should read --in the--;
Col. 14, line 20, "4" at the bottom of the formula isn't in exactly the same spot as in the application;
Col. 14, line 35, "enamtiomer" should read --enantiomer--;
Col. 16, line 1, at the right-hand margin, insert --bIV--;
Col. 16, line 4, "bI" should read --bI.--;
Col. 16, lines 15-20, the structure should be --
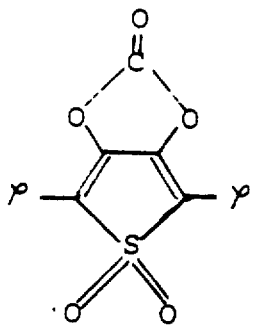
--;

Col. 16, line 30, at the right-hand margin, "V" should read --b V-- AND at the bottom of the formula, "b" should be deleted;
Col. 18, line 55, at the right-hand margin insert --(B2)--;
Col. 24, line 50, that portion of the formula reading "$(CH_2)_nCOOH$" should read --$(CH_2)_nCN$--;

UNITED STATES PATENT AND TRADEMARK OFFICE
CERTIFICATE OF CORRECTION

PATENT NO. : 4,937,346

DATED : June 26, 1990

INVENTOR(S) : Arvidsson et al.

It is certified that error appears in the above-identified patent and that said Letters Patent is hereby corrected as shown below:

Col. 28, line 10, " 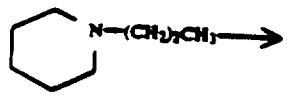 "

should read
--
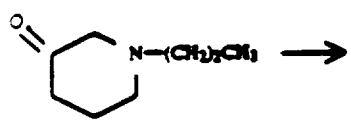

--;

Col. 28, line 52, in the structure,
 should read $(\phi O)_2 PN_3$;

Col. 29, line 12, "preparation" should read --preparations--;
Col. 31, line 64, "(3-oyridyl)" should read --(3-pyridyl)--;
Col. 32, line 25, "(2.05 g)," should read --(2.05 g,--;
Col. 34, line 19, "($K_2CO_33$)" should read --($K_2CO_3$)--;
Col. 34, line 36, "propyloiperidine" should read --propylpiperidine--;
Col. 34, line 47, "yohenyl)" should read --yphenyl--;
Col. 37, line 18, "N -atmosphere" should read --$N_2$-atmosphere--;
Col. 37, line 43, "$NaHCO_33$" should read --$NaHCO_3$--;
Col. 39, line 25, "(C-1.8," should read --(C=1.8,--;

UNITED STATES PATENT AND TRADEMARK OFFICE
CERTIFICATE OF CORRECTION

PATENT NO. : 4,937,346

DATED : June 26, 1990

INVENTOR(S) : Arvidsson et al.

It is certified that error appears in the above-identified patent and that said Letters Patent is hereby corrected as shown below:

Col. 40, line 43, at the top left-side of the table, insert --Intermediates--; and delete "Intermediates" from the body of the table;
Col. 43, line 60, "Aerosil" should read --Aerosil.--;
Col. 45, lines 20-21, "autoreculatory" should read --autoregulatory--;
Col. 48, line 50, "phenylazacycloakanes" should read --phenylazocycloalkanes--;
Col. 50, line 12, "dopminergic" should read --dopaminergic--;
Col. 53, line 24, "strietum" should read --striatum--;
Col. 54, TABLE VI, heading at right, "(cr. table 1)" should read --(cf. table 1)--;
Col. 55, TABLE VI, heading at right, "(cr. table 1)" should read --(cf. table 1)--;
Col. 55, last footnote to Table VI, "apomorphine." should read --apomorphine; differs from control, p<0.001--;
Col. 55, line 35, at the right margin insert --I--;
Col. 55, line 47, "an dR" should read --and R--;
Col. 56, line 40, "2epoxy" should read --2-epoxy--;

Signed and Sealed this

Twenty-second Day of December, 1992

Attest:

DOUGLAS B. COMER

Attesting Officer  Acting Commissioner of Patents and Trademarks